United States Patent [19]

Ohm et al.

[11] Patent Number: 5,784,542
[45] Date of Patent: Jul. 21, 1998

[54] DECOUPLED SIX DEGREE-OF-FREEDOM TELEOPERATED ROBOT SYSTEM

[75] Inventors: Timothy Ohm, La Crescenta; Hari Das, Altadena; Rodriguez Guillermo, La Canada; Curtis Boswell, Pasadena; Eric Paljug, Bridgeville; Paul Schenker, Pasadena; Ed Barlow, San Dimas; Charles Steve, Germantown, all of Calif.

[73] Assignee: California Institute of Technology, Pasadena, Calif.

[21] Appl. No.: 734,967

[22] Filed: Oct. 23, 1996

Related U.S. Application Data

[63] Continuation-in-part of Ser. No. 525,813, Sep. 7, 1995, Pat. No. 5,710,870.

[51] Int. Cl.[6] ............................................. G06F 15/00
[52] U.S. Cl. .................. 395/95; 395/80; 395/82; 395/83; 395/92; 901/27; 901/28; 901/34; 901/36
[58] Field of Search ............................ 395/95, 80, 92, 395/83, 82; 901/27, 28, 34, 36

[56] References Cited

U.S. PATENT DOCUMENTS

| | | | |
|---|---|---|---|
| 4,260,940 | 4/1981 | Engelberger et al. | 318/562 |
| 5,053,975 | 10/1991 | Tsuchihashi et al. | 395/83 |
| 5,086,401 | 2/1992 | Glassman et al. | 395/95 |
| 5,198,736 | 3/1993 | Azuma et al. | 318/568.1 |
| 5,341,459 | 8/1994 | Backes | 395/95 |
| 5,572,999 | 11/1996 | Funda et al. | 128/653.1 |

*Primary Examiner*—George B. Davis
*Attorney, Agent, or Firm*—Michaelson & Wallace

[57] ABSTRACT

The present invention is a low friction, low inertia, six-axis force feedback input device comprising an arm with double-jointed, tendon-driven revolute joints, a decoupled tendon-driven wrist, and a base with encoders and motors. The input device functions as a master robot manipulator of a microsurgical teleoperated robot system including a slave robot manipulator coupled to an amplifier chassis, which is coupled to a control chassis, which is coupled to a workstation with a graphical user interface. The amplifier chassis is coupled to the motors of the master robot manipulator and the control chassis is coupled to the encoders of the master robot manipulator. A force feedback can be applied to the input device and can be generated from the slave robot to enable a user to operate the slave robot via the input device without physically viewing the slave robot. Also, the force feedback can be generated from the workstation to represent fictitious forces to constrain the input device's control of the slave robot to be within imaginary predetermined boundaries.

35 Claims, 20 Drawing Sheets

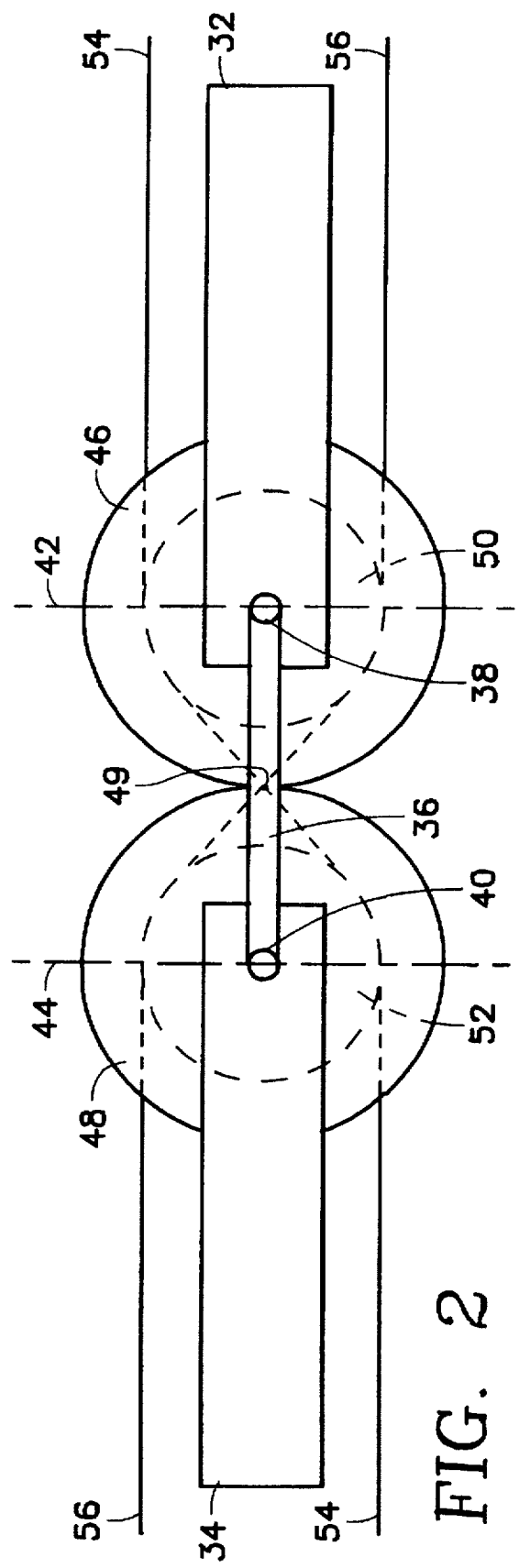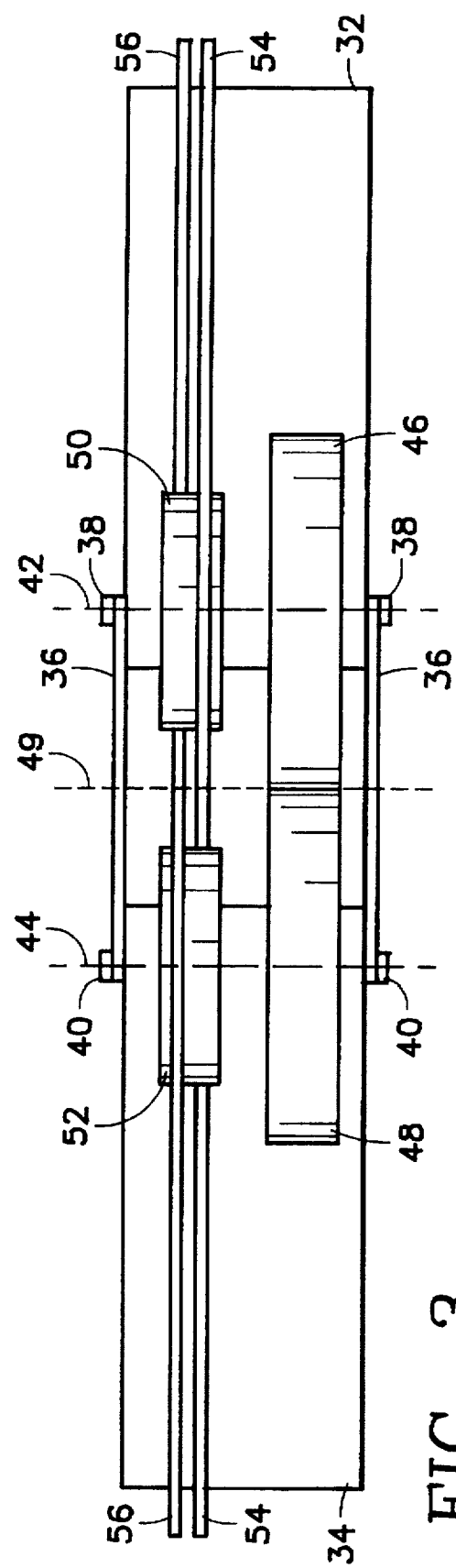
FIG. 2
FIG. 3

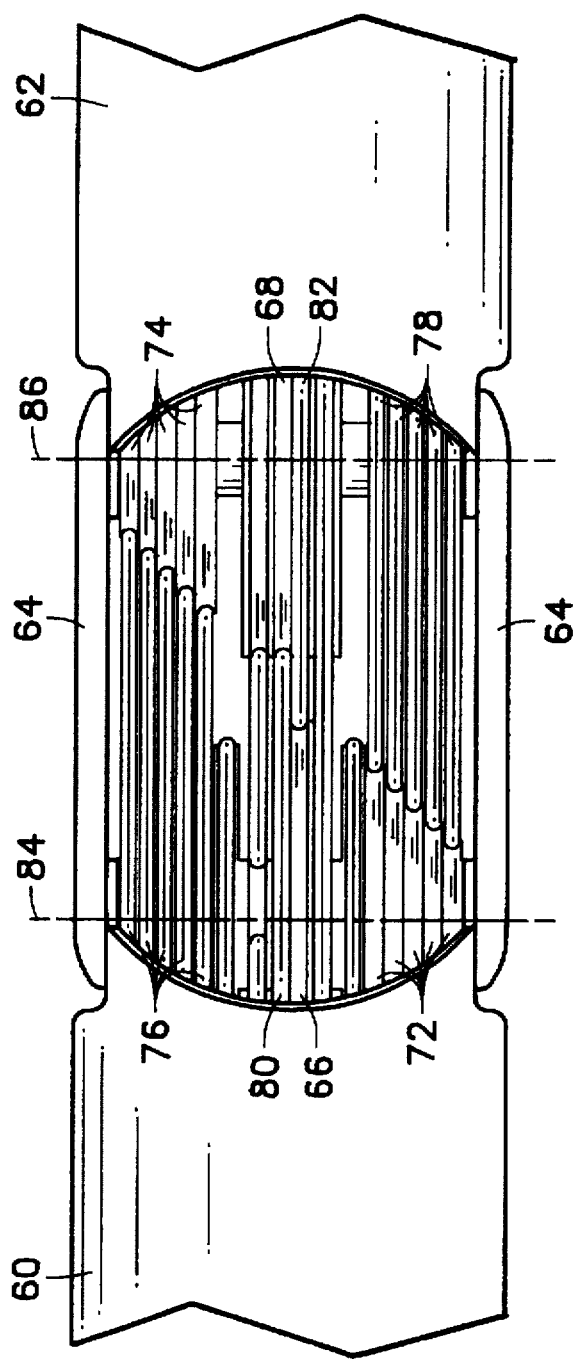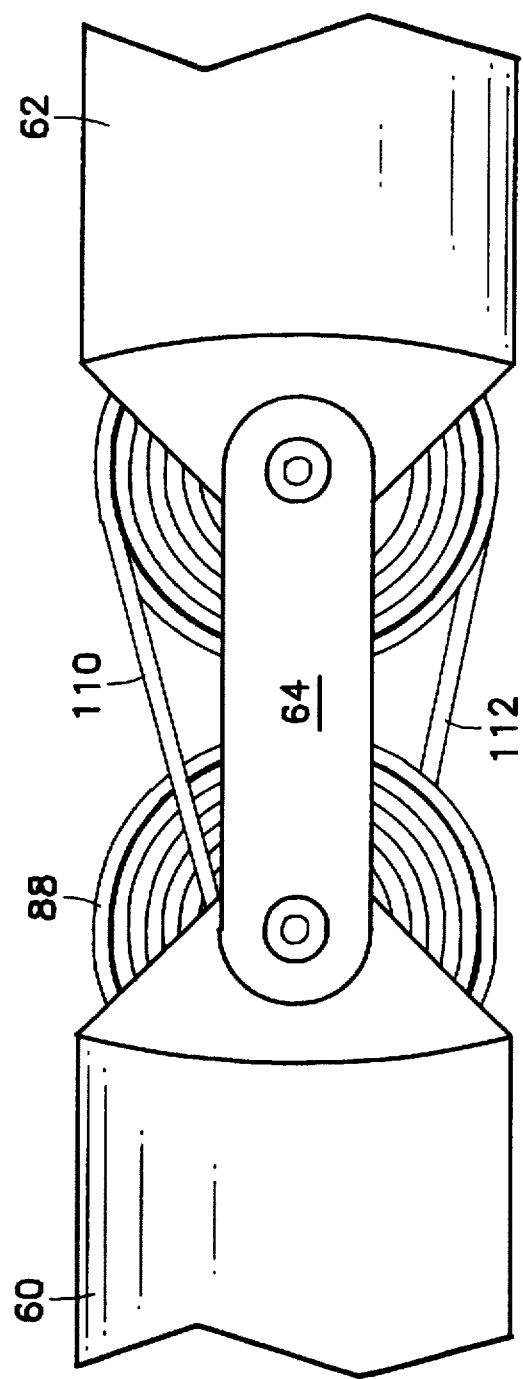
FIG. 4
FIG. 5

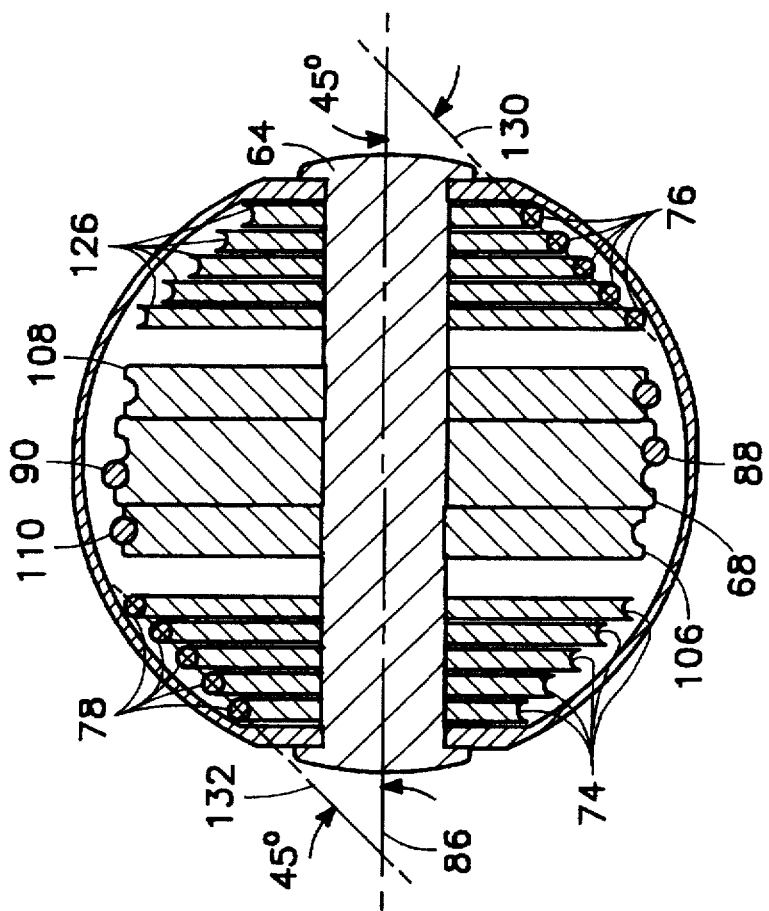
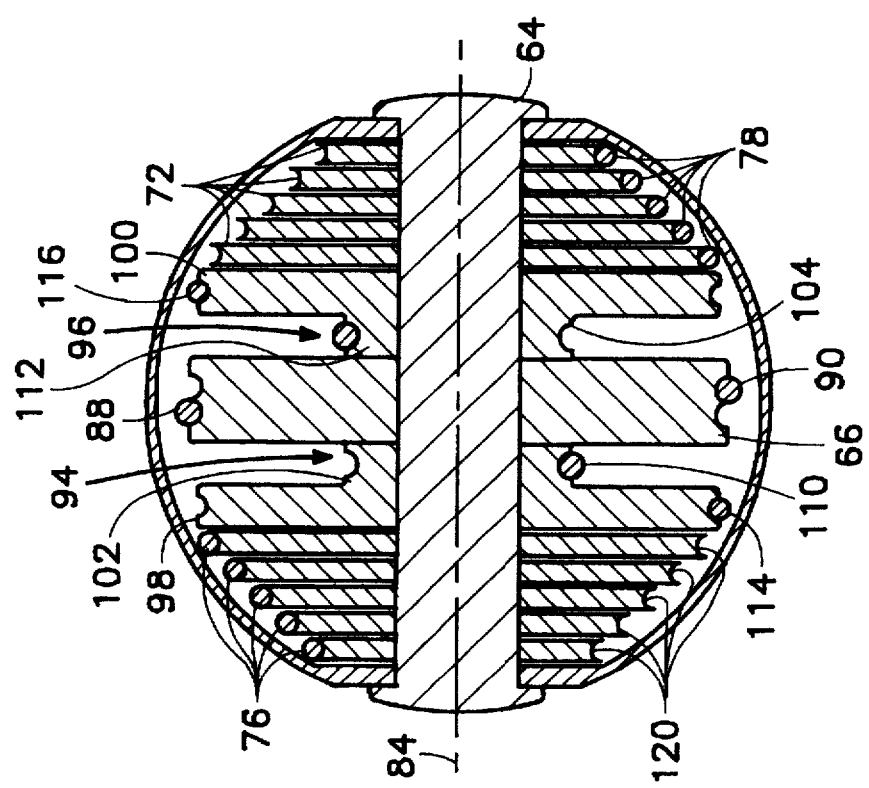
FIG. 8
FIG. 7

DECOUPLED SIX DEGREE-OF-FREEDOM TELEOPERATED ROBOT SYSTEM

CROSS-REFERENCE TO RELATED APPLICATIONS

This application is a continuation-in-part of application Ser. No. 08/525,813 filed Sep. 7, 1995, U.S. Pat. No. 5,710,870.

BACKGROUND OF THE INVENTION

ORIGIN OF THE INVENTION

The invention described herein was made in the performance of work under a NASA contract, and is subject to the provisions of Public Law 96-517 (35 USC 202) in which the contractor has elected to retain title.

1. Field of the Invention

The present invention relates in general to robot manipulators and in particular to a decoupled six degree-of-freedom teleoperated robot system for robot assisted microsurgery.

2. Related Art

Robotic devices are commonly used in factory based environments to complete tasks such as placing parts, welding, spray painting, etc. Examples of robotic systems include U.S. Pat. No. 4,911,033, issued to Rosheim et al., and U.S. Pat. Nos. 4,729,253, 4,723,460, and 4,686,866, issued to Rosheim.

Although these systems are used for a variety of tasks, the Rosheim et al. and Rosheim robotic systems lack important features. For instance, they do not have completely mechanically decoupled axes with passed actuation for transferring actuation through one joint in order to actuate another joint, without affecting the motion of any other joints. In addition, the Rosheim et al. and Rosheim robotic systems are large and bulky and cannot effectively perform small scale tasks, such as microsurgical operations. Also, the Rosheim et al. and Rosheim robotic systems are not tendon-driven systems, and thus, do not have low or zero backlash, which is desirable for microsurgical operations.

Recently, other robotic devices have been used in medical environments to perform surgical operations. Some of these devices include micro-robots having miniaturized end effectors with tendon-driven joints. However, current tendon-driven robot manipulators for small scale microsurgical manipulation suffer from inefficient coupling between joints, inadequate stiffness, packaging problems associated with achieving constant cable path lengths, and activation of multiple joints. In addition, these microsurgical robotic systems do not have force-feedback capabilities.

Also, in many robotic geartrain applications, such as high precision microsurgical operations, zero backlash is desired. Conventional approaches use various antibacklash components, such as high precision connectors and anti-backlash gears, to eliminate backlash in each stage of the geartrain independently. These antibacklash gears are used in each stage and are stacked until the desired gear ratio is achieved. Nevertheless, these conventional approaches are difficult to implement since each stage of the geartrain ideally requires a unique preload (initial loading of the geartrain to snugly 'set' the gears within each other) value. Moreover, preloading is typically tedious and difficult to readjust, if required.

Therefore, what is needed is an input device functioning as a master robot to control a slave robot with passed actuation capabilities, zero backlash, high dexterity, at least six degrees of freedom with all six axes being completely mechanically decoupled, low inertia, low frictional aspects, and force-feedback capabilities.

Whatever the merits of the above mentioned systems and methods, they do not achieve the benefits of the present invention.

SUMMARY OF THE INVENTION

To overcome the limitations in the prior art described above, and to overcome other limitations that will become apparent upon reading and understanding the present specification, the present invention is a decoupled six degree-of-freedom teleoperated robot system for robot assisted microsurgery. The system includes an input device for controlling a slave robot.

The slave robot comprises an arm with double-jointed, tendon-driven revolute joints, a decoupled tendon-driven wrist, and a base with an antibacklash mechanism. The six-axis force feedback input device comprises an arm with double-jointed, tendon-driven revolute joints (similar to the joints of the slave robot) a decoupled tendon-driven wrist with a force/torque sensor, and a base with encoders and motors and an antibacklash mechanism.

A force feedback can be applied to the input device for providing feedback to an operator of the input device. The force feedback can be generated from the slave robot, which the input device controls. Also, the force feedback can be generated from an external device, such as a programmed processor, to produce fictitious forces on the input device. The fictitious forces can represent desired boundaries to constrain the slave robot within.

The input device functions as a master robot manipulator in the microsurgical teleoperated robot system. In the overall system architecture, the slave robot manipulator is coupled to an amplifier chassis. The amplifier chassis is coupled to a control chassis which is coupled to a workstation with a graphical user interface. Also, the amplifier chassis is coupled to the motors of the master robot manipulator and the control chassis is coupled to the encoders of the master robot manipulator. Components of the teleoperated robot system are categorized into a mechanical sub-system, an electronics sub-system, a servo-control sub-system, and a high-level software control sub-system.

Both the master and slave robot manipulators have six degrees of freedom and each include a torso connected to respective actuator bases. Each respective torso is also rotatably coupled to respective arms. Each respective arm comprises two double-jointed robot joints decoupled from each other and a three-axis wrist. The wrist of the slave robot is connected to an end effector and the wrist of the master robot is connected to a stylist.

Each respective set of double-jointed robot joints includes an input link having a first keying drive component and an output link coupled to the input link and having a second keying drive component. The first keying drive component is constrained to rotate with respect to the second keying drive component, thereby defining an instantaneous center of rotation.

In addition, each respective set of double-jointed decoupled joint has a first passing drive component rotatable on the input link and coupled to the actuator of the actuator base. A second passing drive component rotatable on the output link is coupled to the first passing drive component. The first passing drive component rotates with respect to the second passing drive component about the instantaneous center of rotation. The pair of passing drive components are kinematically linked to the keying drive component through the instantaneous center of rotation so that each passing drive component of each respective set of joints is completely mechanically decoupled from the particular joint's motion.

Further, any number of pairs of passing drive components can be used with each decoupled joint as long respective pairs of passing drive components rotate with respect to each other about the instantaneous center of rotation. Moreover, each joint can have an actuation drive component for actuating the particular joint.

The wrist of the master robot is a three axis wrist and has a tendon-driven system with zero backlash in pitch, yaw, and roll axes. The wrist of the master robot utilizes a universal drive component system with dual bearing rings for decoupling the pitch and yaw axes.

The wrist of the slave is a three axis wrist and has a tendon-driven system with three decoupled axes and zero backlash in two of the three axes. The wrist of the slave robot utilizes a dual universal drive component system to provide a three degree-of-freedom, singularity free, mechanically decoupled joint that operates in a full hemisphere of motion (up to 90 degrees in any direction).

Both antibacklash geartrains of the master and slave robots are incorporated between actuators at respective actuator bases and the device to be actuated, such as the output link of a particular respective joint. Both antibacklash mechanisms are multiple stage devices, not limited to any particular number of stages, utilizing a drivetrain system with drive components such as gears, belts, and/or cables. Both antibacklash mechanisms have two independent parallel transmission paths for each drivetrain. The respective drivetrains are mechanically coupled only at an input, such as the motor, and an output, such as an actuation pulley located on a particular joint. Both system allow convenient preloading of all the stages simultaneously.

Features of the teleoperated microsurgical robot of the present invention include double-jointed robot joints, at least six degrees of freedom with all six axes completely mechanically decoupled, decoupled passed actuation, zero backlash in the wrist, and force-feedback capabilities. Advantages of the teleoperated microsurgical robot of the present invention is that it is extremely sensitive and small, has high dexterity, has low inertia, and has low frictional aspects.

The foregoing and still further features and advantages of the present invention as well as a more complete understanding thereof will be made apparent from a study of the following detailed description of the invention in connection with the accompanying drawings and appended claims.

BRIEF DESCRIPTION OF THE DRAWINGS

Referring now to the drawings in which like reference numbers represent corresponding parts throughout:

FIG. 2 illustrates a side view of the general decoupled robot joints of the present invention;

FIG. 3 illustrates a top view of FIG. 2;

FIG. 4 illustrates a top view of one embodiment of the decoupled joints with cable driven actuation;

FIG. 5 illustrates a side view of FIG. 4;

FIG. 7 illustrates a cross sectional side view of the input link of FIG. 4;

FIG. 8 illustrates a cross sectional side view of the output link of FIG. 4;

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Input Device Overview

Figure 1B:
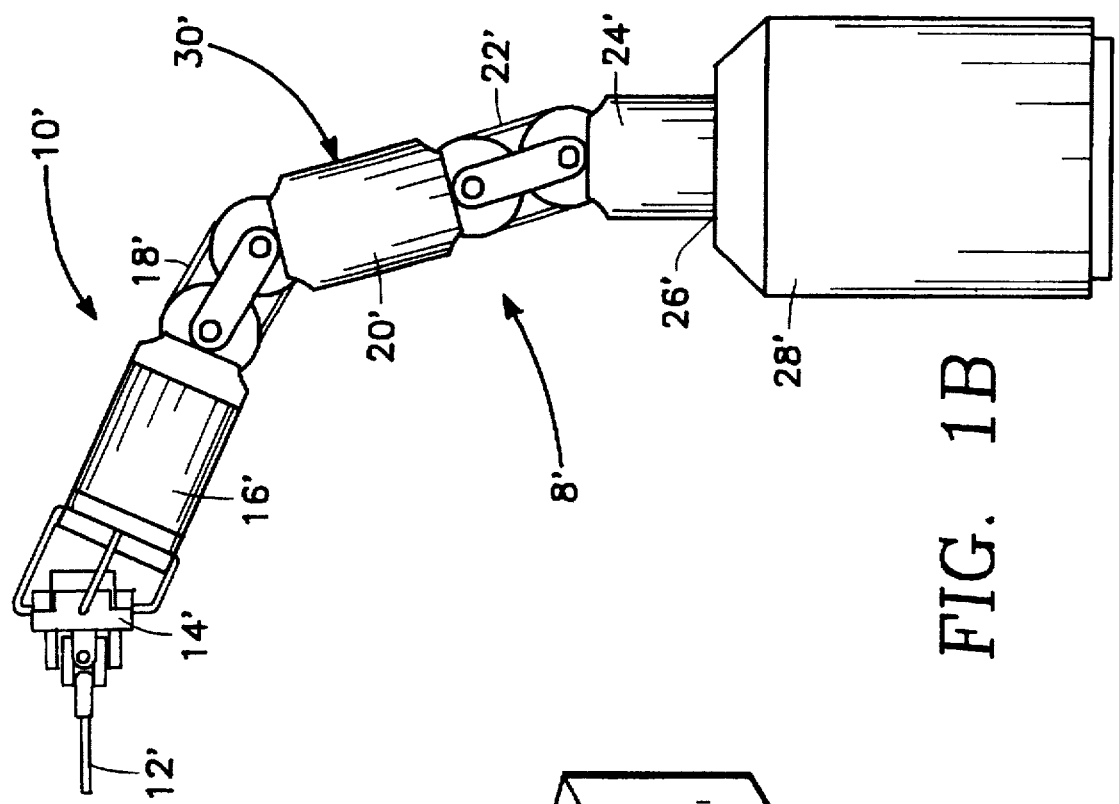
FIG. 1B illustrates an overall view of the slave robot of the present invention.
Figure 1A:
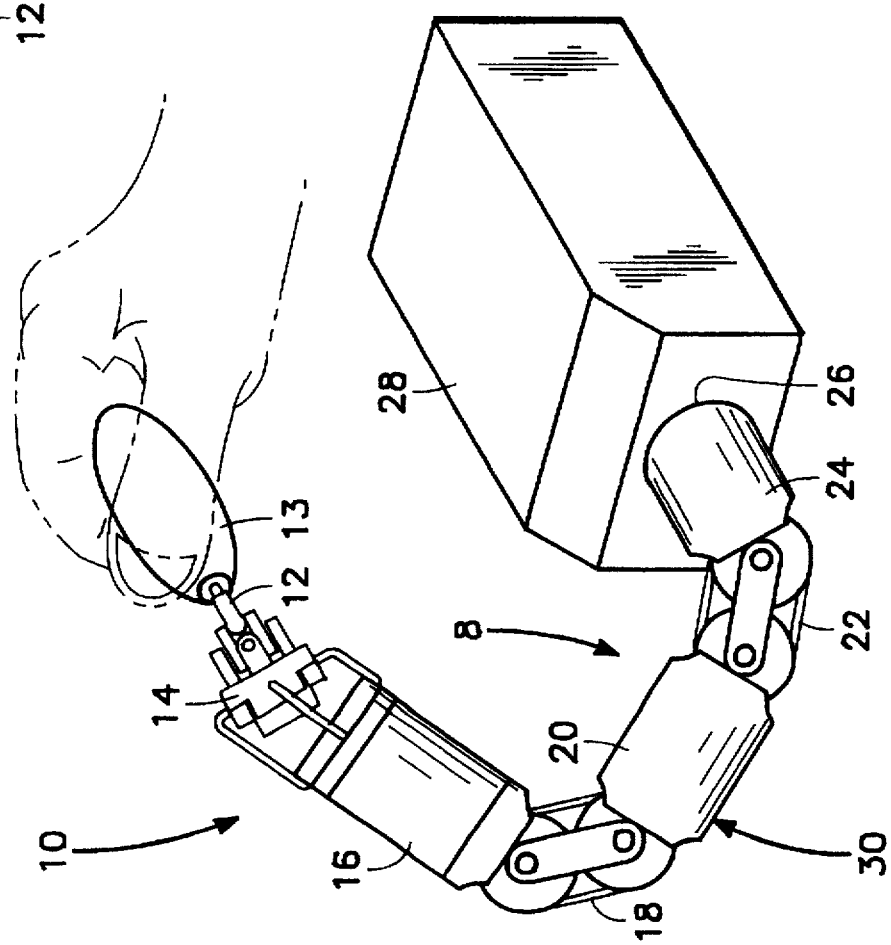
FIG. 1A illustrates an overall view of the master robot of the present invention.

FIG. 1A illustrates an overall view of the master robot or input device of the present invention. FIG. 1B illustrates an overall view of the slave robot of the present invention. In the preferred embodiment, the input device 8 functions as a master robot manipulator for a microsurgical teleoperated robot system for controlling the movement of a slave robot manipulator 8'.

Referring to FIG. 1A, the input device 8 or master robot manipulator comprises an arm 10 coupled to a wrist 14. The wrist 14 is coupled to a six-axis force/torque sensor 12 which is coupled to a stylist 13 located outboard of the sensor 12. The wrist 14 provides an intersecting axis for pitch, yaw, and roll and is coupled to a forearm 16 which is coupled to a doubled-jointed elbow joint 18 for connecting an upper arm 20 to the forearm 16. The upper arm 20 is coupled to a double-jointed shoulder joint 22 for connecting a shoulder 24 to the upper arm 20. The shoulder 24 is coupled to a torso joint 26 which is coupled to an actuator base 28.

The actuator base 28 contains an antibacklash mechanism and electrical and mechanical components for receiving input from the input device 8 and transmitting the input for teleoperation. The electrical and mechanical components receive feedback from an external device, such as a programmable processor or a torque sensor located on the slave robot of FIG. 1B, which is controlled by the input device 8. The electrical and mechanical components transmit the feedback to the input device 8.

The forearm 16, upper arm 20, and shoulder 24 all preferably have housings in the form of cylindrical casings 30. The torso joint 26 is rotatable relative to the actuator base 28. The wrist joint 12 has three degrees of freedom and each joint (elbow 18, shoulder 22, and torso 26) has one degree of freedom.

In addition, the input device 8, functioning as a master robot 8, has indexing capabilities. For example, during operation of the system, if the master robot 8 reaches its physical end of travel or its range of motion has reached its boundaries, but the slave robot of FIG. 1B requires further movement, the master robot 8 can be temporarily deactivated, relocated within its boundaries, and then reactivated to provide the additional movement required by the slave. Thus, the master robot 8, operating in a limited space area, can control the movement of the slave robot within an infinite area, restricted only by the physical limitations of the system.

Referring to FIG. 1B, the slave robot manipulator 8' has six degrees of freedom and includes an arm 10' with an end effector 12' coupled to a three-axis wrist joint 14', which is coupled to a forearm 16'. The forearm 16' is coupled to a doubled-jointed elbow joint 18' for connecting an upper arm 20' to the forearm 16'. The upper arm 20' is coupled to a double-jointed shoulder joint 22 for connecting a shoulder 24' to the upper arm 20'. The shoulder 24' is coupled to a torso joint 26' which is coupled to an actuator base 28'.

The actuator base 28' contains electrical and mechanical components for controlling the movements of the robot 8'. The forearm 16', upper arm 20', and shoulder 24' all preferably have housings in the form of cylindrical casings 30'.

The torso joint 26' rotates the arm 10' relative to the actuator base 28'. The wrist joint 14' has three degrees of freedom and each joint (elbow 18', shoulder 22', and torso 26') has one degree of freedom.

The double-jointed robot joints 18, 18', 22, 22' and the wrist joints 14, 14' of FIGS. 1A and 1B can be used in large automated environments, as well as micro automated environments, including microsurgical environments. The double-jointed robot joints 18, 18', 22, 22' will be discussed in detail below in FIGS. 2–10, the wrist joints will be discussed in detail below in FIG. 11, one antibacklash system will be discussed in detail below in FIGS. 12A and 12B, and the master and slave robots will be discussed in FIGS. 14A, 14B, 14C, and 14D. The entire robot system will be described in detail in FIGS. 15–32 below. Although the robot manipulator can be used in numerous environments, the preferred embodiment involves the use of the robot manipulator in a microsurgical environment.

Double-Jointed, Decoupled Joints

FIG. 2 is a side view and general overview of a double-jointed, decoupled robot joint of the master or slave robot of the present invention. FIG. 3 illustrates a top view of FIG. 2. The double-jointed robot joint couples sections of respective robots 8, 8' of FIG. 1A and 1B together. Each double-jointed robot joint can have internal actuators, such as an internal actuation pulley/cable system (described in detail in FIGS. 4–8) coupled to external motors located at the respective actuator bases 28, 28' of FIG. 1A and FIG. 1B or internal motors in each joint (not shown) for actuating the particular joint or other joints of the respective robots 8, 8'.

The double-jointed robot joint of FIGS. 2 and 3 includes an input link 32 and an output link 34. The input link 32 is on the near side of the actuator base 28 while the output link 34 is on the far side of the actuator base 28 and is moveable relative to the input link 32. The input and output links 32, 34 are attached to each other via a pair of hinged side struts 36. The links 32, 34 pivot about pivot points 38 and 40 at the input link 32 and output link 34, respectively. These pivot points 38 and 40 define an input axis 42 and output axis 44, respectively.

An input keying drive component 46 and an output keying drive component 48 are centered on each respective hinged axis or pivot point 38 and 40 and are attached to each respective link 32 and 34 so that they are constrained to rotate with respect to each other. This constrained rotation between the input keying drive component 46 and the output keying drive component 48 defines an instantaneous center of rotation 49 between the two keying drive components 46 and 48. The keying drive components 46 and 48 can be fixed spur gears which mesh together or they can be fixed pulleys with wound cables as described in detail below.

In addition, each joint has an input passing drive component 50 rotatable about the pivot point 38 of the input link 32. The input passing drive component 50 is coupled to an actuator (not shown) at the actuator base 28 of FIG. 1 and to an output passing drive component 52. The output passing drive component 52 is rotatable about the pivot point 40 of the output link 34. The passing drive components 50 and 52 can be a spur gear system or a pulley system. In a pulley system, respective passing cables passing through each respective passing drive component would be included.

For example, a first passing cable 54, originating from another passing drive component in another joint or from the actuator base 28 of FIG. 1, travels from the input link 32, around the top of the input passing pulley 50, through the instantaneous center of rotation 49, and then around the bottom of the output passing pulley 52. A second passing cable 56, originating from the same location as the first passing cable 54, travels from the input link 32, around the bottom of the input passing pulley 50, through the instantaneous center of rotation 49, and then around the top of the output passing pulley 52.

This arrangement allows the input passing drive component 50 to rotate with respect to the output passing drive component 52 about the same instantaneous center of rotation 49 defined by the input and output keying drive components 46 and 48. Since the pair of passing drive components rotate about the same instantaneous center of rotation 49 as the keying drive components 46 and 48, the passing drive components 50 and 52 are kinematically decoupled from the joint's motion. This decoupling configuration allows the passing drive components 50 and 52 to actuate movement in other joints without affecting the motion of the particular joint.

Further, any number of pairs of passing drive components can be used with each joint as long as coupled pairs of passing drive components (input and output) rotate with respect to each other about the same instantaneous center of rotation defined by the keying drive components.

Double-Jointed Tendon-Driven Decoupled Joints

FIGS. 4-10 show a tendon-driven system of one embodiment of the double-jointed decoupled robot joints. FIG. 4 is a top view and FIG. 5 is side view of tendon-driven double-jointed decoupled robot joints. The joint of FIG. 4 is structurally similar to the joint of FIGS. 2 and 3 and includes an input link 60, an output link 62, hinged side struts 64, an input keying drive component 66, an output keying drive component 68, an instantaneous center of rotation 70 (shown in FIG. 6), input passing drive components 72, output passing drive components 74, and corresponding passing cables 76 and 78, respectively.

The functions of each element above has the same or similar functions as the related elements of FIGS. 2 and 3. However, the embodiment of FIGS. 4-10 is different in that it is a cable or tendon-driven system and further includes an actuation mechanism. Since the embodiment of FIGS. 4-10 is a cable or tendon-driven robot, the keying drive components 66 and 68 are pulleys with corresponding cables 80 and 82, respectively, which can be stainless steel cables. Also, FIGS. 4-10 further include actuation pulleys and cables within the particular joint for actuating the joint.

The input keying pulley 66 is fixed to the input link 60 and the output keying pulley 68 is fixed to the output link 62 on respective input and output axes 84 and 86. The input axis 84 is defined by a pivot point of the input keying pulley 66 on the input link 60. An output axis 86 is the counterpart to the input axis 84 and is defined by a pivot point of the output keying pulley 68 on the output link 62.

Figure 6:
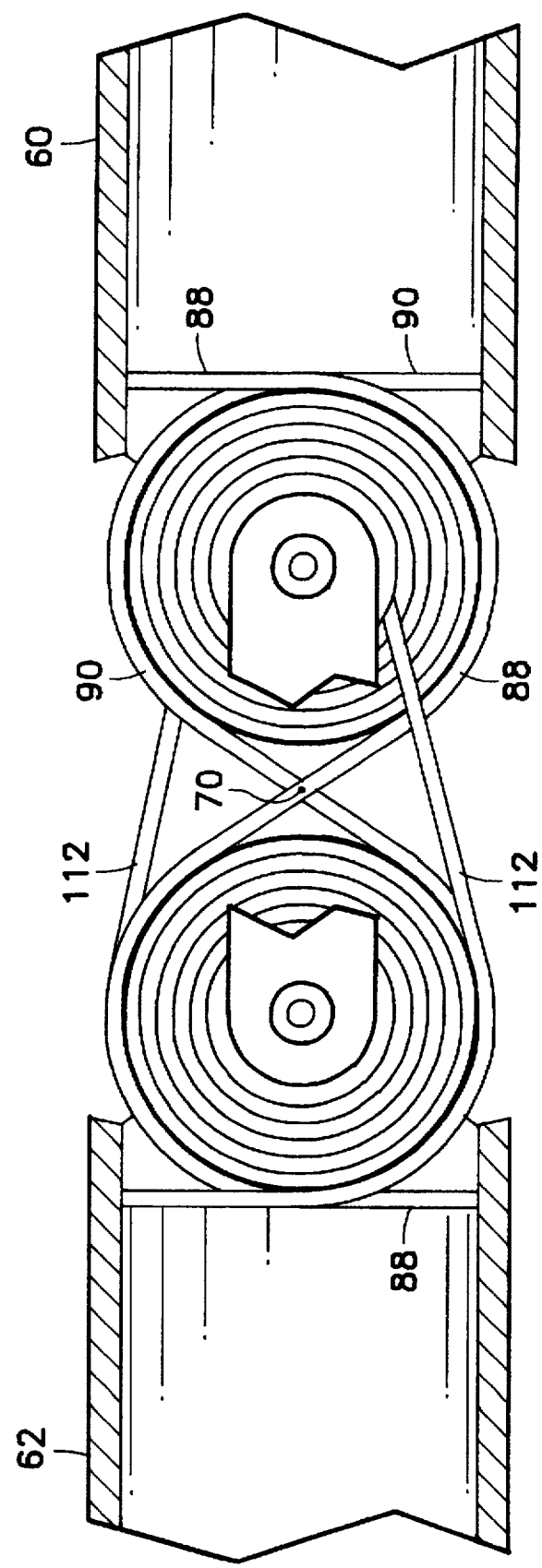
FIG. 6 illustrates a cut-away side view of FIG. 5.

Referring to FIG. 6, two keying cables 88 and 90 are connected to the input link 60 and the output link 62, respectively. The keying cables 88 and 90 can also be connected directly to the keying pulleys 66 and 68, respectively. The first keying cable 88 is attached to a bottom portion of the input link 60 and winds around a top side of the input keying pulley 66, crosses to the output keying pulley 68, winds around a bottom side of the output keying pulley 68, and terminates on a top portion of the output link 62.

The second keying cable 90 is attached to a top portion of the input link 60 and winds around a bottom side of the input keying pulley 66, crosses to the output keying pulley 68, winds around a top side of the output keying pulley 68, and terminates on a bottom portion of the output link 62. The second keying cable 90 traverses a mirrored path of the first keying cable 88. If the cables are stainless steel, the cables 88 and 90 can be terminated with solder joints or crimp terminations. However, soldered terminations are preferred because they are easy to install, take up very little space, and do not inflict an initial stress concentration in the cable, assuming the solder joint is not flexed.

The keying pulleys are constrained to respective links similar to the keying drive component arrangement of FIGS. 2 and 3. Also, the keying pulleys 66 and 68 preferably have the same diameter, but this is not necessary. One feature of the present invention is that the keying cables 88 and 90 cross one another between the keying pulleys 66 and 68 as shown in FIG. 6 to define the instantaneous center of rotation 70. The identical effect of having an instantaneous center of rotation can be achieved with spur gears which mesh together, in a similar manner as the keying drive components 46 and 48 of FIGS. 2 and 3. Although, keying spur gears would introduce backlash into the robot manipulator, backlash can be prevented in the tendon-driven system by a standard single stage antibacklash system or in accordance with the antibacklash system described in detail in FIGS. 14A and 14B. Thus, the present invention is preferably a tendon-driven system consisting of keying cables 88 and 90 and keying pulleys 66 and 68 instead of spur gears.

Figure 9:
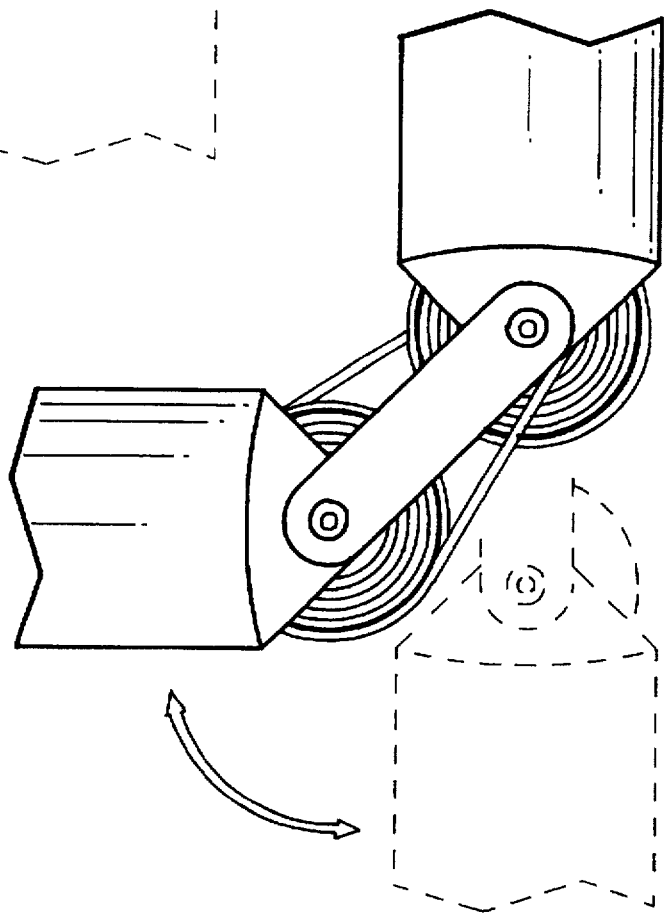
FIG. 9 illustrates a 90 degree deflection of the robot arm connected to the decoupled joint of the present invention.

Each double-jointed robot joint has one degree of freedom. Each joint's rotation is dependant on the ratio of the keying pulleys' 66 and 68 diameters. For example, if both keying pulleys 66 and 68 have the same diameter, the angle that the output link 62 is moved relative to the input link 60 will be exactly twice the angle between the side struts 64 and each link 60 and 62. In other words, if the output link 62 is rotated 90° to the input link 60, the side struts 64 will rotate 45° to each link 60 and 62, as shown in FIG. 9. Likewise, the output link 62 can rotate up to 180° at which point the side struts 64 will be at 90° to each link 60 and 62, as shown in FIG. 10.

Figure 10:
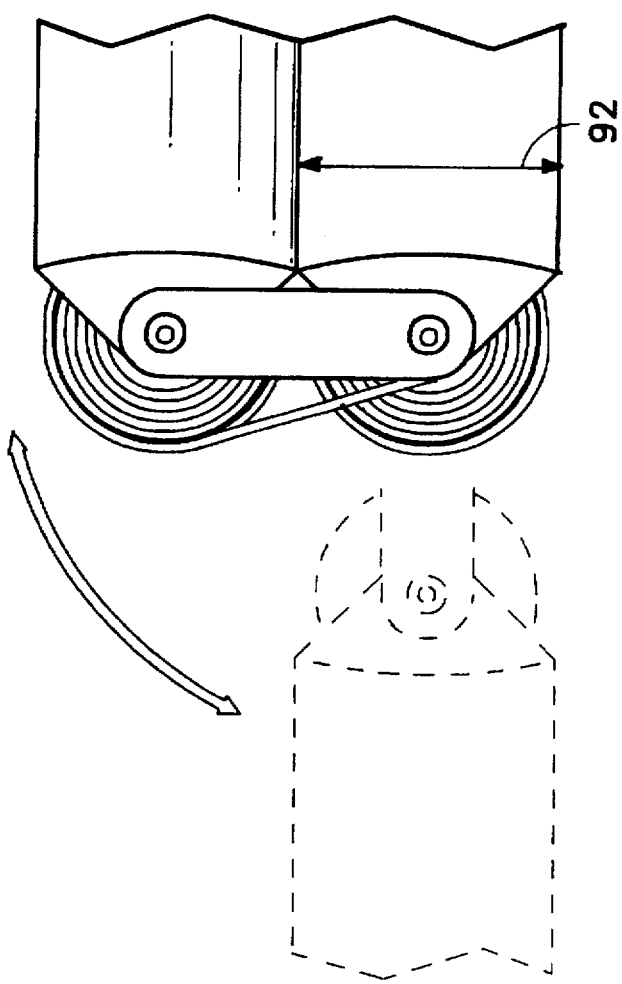
FIG. 10 illustrates a 180 degree deflection of the robot arm connected to the decoupled joint of the present invention.

In order to achieve the maximum 180° rotation, the distance between the input and output axes must be at least equal or greater than an effective diameter 92 of each links 60 and 62, as shown in FIG. 10. It is important to note that the 180° range of motion is bidirectional, thus the full range of joint motion is 360°. Alternatively, if the keying pulleys 66 and 68 have different diameters, other kinematic relationships can be achieved between the input link 60, output link 62, and side struts 64 without affecting other features of the robot.

FIGS. 7 and 8 are cross-sectional views through the input and output axes, respectively. The joint can be actuated by two input dual actuation pulleys 94 and 96. Each input dual actuation pulley 94 and 96 includes transmission pulleys 98 and 100 and connecting pulleys 102 and 104, respectively. The two input dual actuation pulleys 94 and 96 sandwich the input keying pulley 66 on the input axis 84 as shown in FIG. 7. The actuation pulleys 94 and 96 rotate independently of the input keying pulley 66.

Also, two output actuation pulleys 106 and 108 sandwich the output keying pulley 68 on the output axis 86 as shown in FIG. 8. Referring to both FIGS. 7 and 8, each of the connecting pulleys 102 and 104 have corresponding actuation cables 110 and 112 terminated to it. Also, the transmission pulleys 98 and 100 have transmission cables 114 and 116 coupled to the actuator base for actuating the pulleys 94 and 96.

Referring to FIGS. 6–8, the first actuation cable 110 can be terminated to a top side of the connecting pulley 102 of the first input actuation pulley 94 and the second actuation cable 112 can be terminated to a bottom side of the connecting pulley 104 of the second input actuation pulley 96. The first actuation cable 110 travels from the first input actuation pulley 94, winds around a top side of the first output actuation pulley 106, and terminates to a bottom side of the output link 62. The second actuation cable 112 travels from the second input actuation pulley 96, winds around a bottom side of the second output actuation pulley 108, and terminates to a top side of the output link 62. Connecting pulleys 102 and 104 can have the same diameters of actuation pulleys 106 and 108, but this is not necessary. The transmission cables 114 and 116 are coupled to the transmission pulleys 98 and 100 of the input actuation pulleys 94 and 96, respectively, to actuate the output actuation pulleys 106 and 108 through the connecting pulleys 102 and 104 via the actuation cables 110 and 112.

Motors typically operate at high speeds with low torque. However, actuation of the robot joints by motors located at the actuator base typically requires the motor to have low speed with high torque. Gear reduction at the joints resolves this problem by reducing a motor's high speed with low torque to low speed with high torque. The actuation pulleys 106 and 108 can incorporate gear reduction at the joints. For example, if the connecting pulleys 102 and 104 of the input actuation pulleys 94 and 96 have the same diameters, and the output actuation pulleys 106 and 108 have the same diameters, and the connecting pulleys 102 and 104 have different diameters from the output actuation pulleys 106 and 108, a resultant gear reduction ratio for the particular joint will be created.

The resultant gear reduction ratio between the input actuation pulleys 94 and 96 and the output actuation pulleys 106 and 108 is given by:

$$RATIO = \frac{1}{2}(1+d_o/d_i)$$

where $d_o$ is the diameter of the output actuation pulleys 106 and 108 and $d_i$ is the diameter of the connecting pulleys 102 and 104 of the input actuation pulleys 94 and 96. This relationship also assumes that both keying pulleys 66 and 68 have the same diameter. Therefore, if the ratio of the diameters of the output actuation pulleys 106 and 108 to the diameters of the connecting pulleys 102 and 104 of the input actuation pulley is 3:1, the resultant gear ratio for the joint will be 2:1 (the output actuation pulley revolves once for every two revolutions of the input actuation pulley).

Also, gear reduction in close proximity to the joint increases stiffness. Typically, stiffness of a tendon-driven mechanism is directly related to the spring constant of the cable or tendon. Thus, high stiffness is achieved by a high spring constant. In addition, the spring constant is inversely proportional to the cable or tendon length. Hence, short cable paths will yield a high spring constant which in turn produces high stiffness. Relatively high stiffness can be achieved with relatively larger diameter cables or tendons.

A resultant gear reduction ratio of 2:1 will produce a short actuation cable length and relatively high stiffness in the transmission cables 114 and 116. The stiffness is related to the resultant gear ratio by a factor of the resultant gear ratio squared. Thus, the diameter of the transmission cables 114 and 116 can be small, thereby enabling small bend radii and more compact packaging.

Similar to the keying drive components of FIGS. 2 and 3, the actuation pulleys/cables can be a spur gear arrangement which would further increase stiffness. However, unlike the keying drive components 48 and 50 of FIGS. 2 and 3, the use of spur gears with dual transmission path cables 114 and 116 (two transmission paths from the actuator) for the actuation pulleys/cables would not induce backlash into the robot manipulator system. This is because the dual transmission paths are tied together at the actuator of the actuator base of FIG. 1 and the output link only. For example, as a result of the actuation pulley arrangement, the tension in the transmission paths defined by the transmission cables 114 and 116 will automatically preload the actuation cables 110 and 112. Further, if the actuation cables 110 and 112 were replaced with a spur gear train, preloading would likewise occur due to this dual transmission path arrangement.

Referring to FIGS. 4, 7, and 8, the joint of the robot manipulator of the present invention also includes an idler pulley/passing cable system. Passing cables 76 and 78 of passing pulleys 72 and 74 pass through a particular joint to actuate other joints of the robot manipulator, thereby mechanically decoupling the particular joint's motion from the other joints' motion. The passing cables 76 and 78 pass through the joint over input idler pulleys 120 and output 126 idler pulleys. The input idler pulleys 72 and 120 and output idler pulleys 74 and 126 rotate freely about the input axis 84 and output axis 86, respectively. The robot can have an unlimited number of idler pulleys and corresponding passing cables.

In order effectuate complete decoupling from the particular joint's motion to other joints' motion, two constraints must be met. First, for a given passing cable 78, corresponding input 72 and output 74 idler pulleys must have the same diameter ratio as that of the input 66 and output 68 keying pulleys, respectively. For example, if the keying pulleys 66 and 68 have equal diameters (1:1 ratio), the idler pulleys 72 and 74 for a corresponding passing cable 78 must have equal diameters (1:1 ratio), or coupling will occur. The absolute size of the idler pulleys 72 and 74 have no consequence.

The second constraint is that the passing cables 78 must follow the same path as the keying cables 88 and 90 and define the same instantaneous center of rotation 70 as the keying cables 88 and 90. Namely, the passing cables 78 must cross from the idler pulleys 72 on input axis 84 to the idler pulleys 74 on the output axis 86 at the same location the keying cables 88 and 90 cross. As a result, as the joint rotates, the amount of passing cable 78 that is wound onto one idler pulley 72 on the input axis 84 equals the amount of passing cable 78 that is unwound off the idler pulley 74 on the output axis 86.

Also, since the keying pulleys 66 and 68 do not rotate relative to their corresponding links 60 and 62, and the passing cables 78 are cabled via the same scheme as the keying cables 88 and 90, the idler pulleys 72 and 74 are stationary relative to the links 60 and 62. This produces complete decoupling of the joint and the passing cables 78. Further, there is no restriction (other than physical packaging) to the amount of passing cables 78 that can be passed through a particular joint.

In addition, the passing cables 78 path lengths are constant throughout the entire range of travel. Depending on the idler pulley 72 and 74 diameters, it may be necessary to confine the passing cables 78 to prevent lifting off their corresponding idler pulleys 72 and 74. Confinement can be accomplished by wrapping the passing cables 78 completely around the corresponding idler pulleys 72 and 74, or by adding idler pulleys (not shown) inside the links 60 and 62.

If adjacent joints are to be moved perpendicular to one another (the output link of one joint attaches to the input link of another joint such that the resulting output and input axes are perpendicular), two additional constraints on the passing cables 78 are necessary. The first constraint is that two sets of independent idler pulleys, each consisting of an input idler pulley and an output idler pulley, are needed for each path of cable. The second constraint is that the passing cables 78 must be arranged in such a way that they will align to idler pulleys on the next perpendicular joint. In other words, all the passing cables 78 on their respective idler pulleys of a particular joint must align smoothly onto the idler pulleys of a connecting joint.

For example, FIGS. 7 and 8 illustrate one embodiment to achieve smooth alignment. A first set of passing cables 78 are arranged on incrementally smaller idler pulleys to form a 45° imaginary line 132 on one side of the keying pulley. Likewise, a second set of passing cables 76 are symmetrically arranged on incrementally smaller idler pulleys about the joint's center to form a 45° imaginary line 130 on an opposite side of the keying pulley. As a result, the joint can be rotated at 90° increments and still align with the previous joint. Other angular increments can be achieved by positioning the passing cables in other configurations as long as all the passing cables on their respective idler pulleys of a particular joint are aligned smoothly onto the idler pulleys of a connecting joint.

Decoupled Tendon-Driven Wrist

Figure 11:
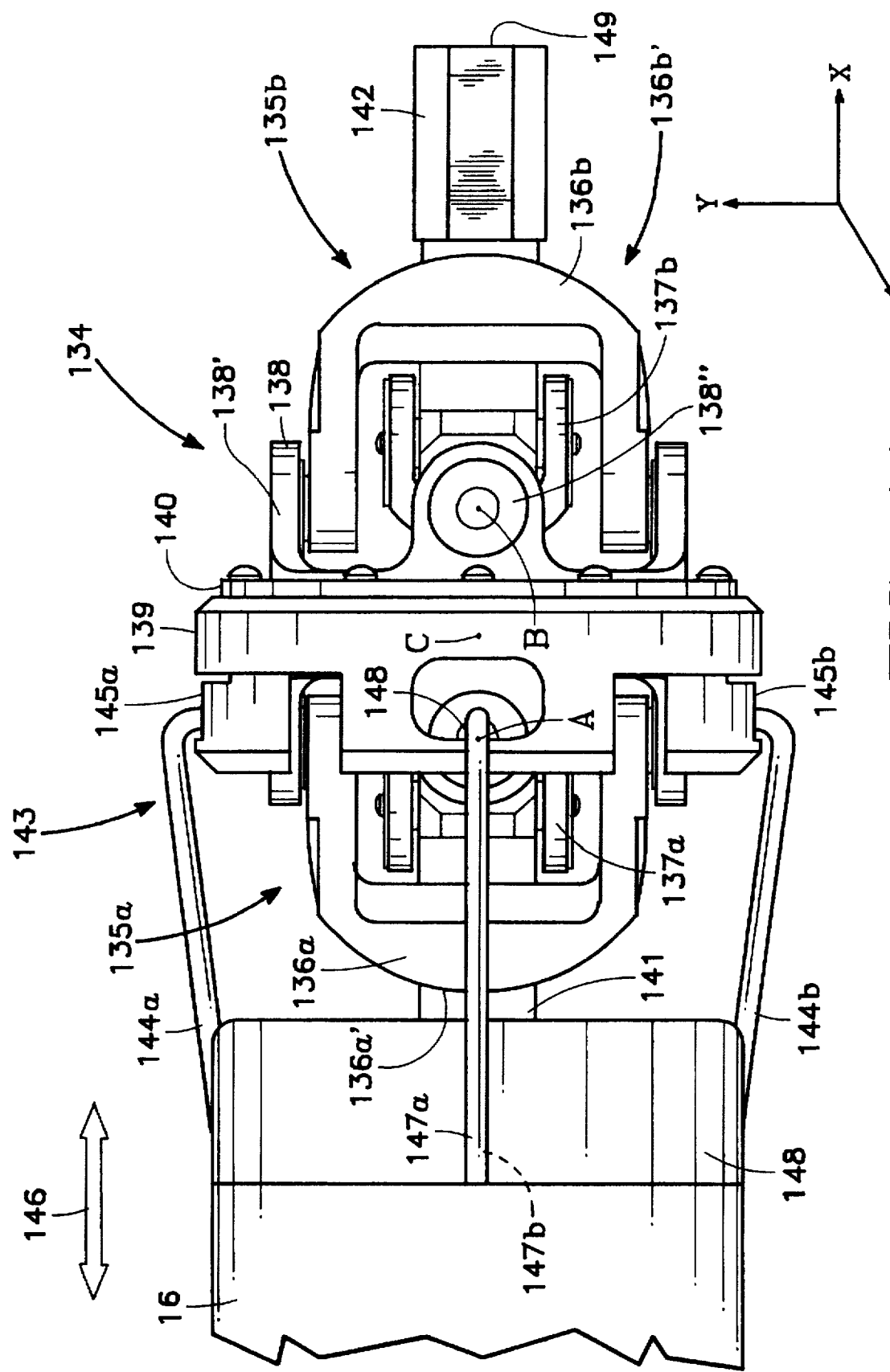
FIG. 11 illustrates one robot wrist which can be utilized as the preferred wrist for the slave robot 8 and an alternate wrist for the master robot.

FIG. 11 illustrates one robot wrist which can be utilized as the preferred wrist for the slave robot 8 and an alternate wrist for the master robot. In the preferred embodiment for the slave robot 8' of FIG. 1B, the robot wrist 134 includes an input assembly 135A, an output assembly 135B, an inner housing 138, an outer housing 139, a middle housing 140, an input shaft 141, an output shaft 142, and a linkage assembly 143. The input and output assemblies 135A, 135B define a dual universal joint system that provides a three degree of freedom, singularity free, mechanically decoupled joint that operates in a full hemisphere of motion (up to 90 degrees in any direction).

The input assembly 135A includes an input outer universal 136A and an input inner universal 137A. Likewise, the output assembly 135B includes output outer and inner universals 136B, 137B which are counterparts of the input universals 136A, 137A. Each input universal 136A, 137A is symmetrical to its output universal 136B, 137B counterpart, respectively. The corresponding counterparts, defined by the symmetrical arrangement, are rotatably coupled to each other. The input and output universals are preferably coupled to each other by a tendon or cable arrangement (not shown) along a longitudinal axis parallel to an x axis.

Specifically, the universals are U-shaped and have arcuate faces on opposing input and output sides. The U-shaped configuration of the outer universals 136A, 136B define a respective slot for slidably receiving the input and output shafts 141, 142, respectively. Both outer and inner universals terminate in a pair of the arcuate faces. The arcuate faces have holes (not shown) for mounting the cables (not shown) between respective input and output outer universals 136A, 136B. Similarly, each inner universal 137B, 137B terminates in a pair of the arcuate faces. The inner universal faces also have holes (not shown) for mounting the cables (not shown) between respective input and output inner universals 137B, 137B. Thus, the input universals 136A, 136B rotate on the respective arcuate faces about the output universals 137B, 137B, to define an instantaneous center.

The tendon or cable coupling arrangement of each set of universals is functionally similar to the keying pulley/cable arrangement of FIGS. 4–8. For example, the input universals 136A, 137A are fixed to an input origin A and the output universals 136B, 137B are fixed to an output origin B. Each input and output origin, A, B, consist of two orthogonal axes about the y and z axes. A set of outer universal cables (not shown) couples the input outer universal 136A to the output outer universal 136B. Likewise, a set of inner universal cables (not shown) couples the input inner universal 137A to the output inner universal 137B. The outer universal set of cables is aligned perpendicularly to the inner universal set of cables. The outer and inner universal cables are preloaded (in accordance with the discussion below in FIGS. 14A and 14B) in order to eliminate backlash in the y and z axes. The outer and inner universal cables are preferably steel cables.

Also, each pair of coupled universals rotate with respect to one another about a defined instantaneous center, similar to the input and output keying pulley arrangement of FIGS. 4–8. However, the instantaneous center of FIG. 11 has two axes of rotation, namely the y and z axes, unlike the instantaneous center of FIGS. 4–8 which has only one axis or rotation. The rotational movements of the universals about their respective axes will be discussed below in detail.

The inner housing 138 has two halves, each being defined by two pairs of symmetrical crowns 138', 138". Each crown 138', 138" has four holes (not shown) centered on respective input and output origins A, B. The input universals 136A, 137A are rotatably mounted in the holes in each crown 138', 138" on the input origin A via bearings (not shown). The output universals 136B, 137B are rotatably mounted in the holes in each crown 138', 138" on the output origin B via bearings. When mounted in the inner housing 138, the input universals 136A, 137A rotate while constrained to the input origin A, and the output universals 136B, 137B rotate while constrained to the output origin B.

The output shaft 142 is rotatably coupled to the output inner universal 137B at the origin point B at the inner housing 138. The input shaft 141 is rotatably coupled to the input inner universal 136A at the input origin point A at the inner housing 138. This arrangement enables rotation of the input and output shafts 141, 142 about the y axis. The input and output shafts 141, 142 are coupled to the input and output inner universals 137A, 137B, respectively, with bearings (not shown). The inner universals 137A, 137B are rotatably coupled to the inner housing 138 at the z axis.

The output shaft 142 slides within the slot defined by the U-shaped configuration of the output outer universal 136B along the y axis. The input shaft 141 slides within the slot defined by the U-shaped configuration of the input outer universal 136A along y axis. This arrangement enables the input shaft 141 to rotate around the z axis and move the output inner universal 137B. Rotation of output shaft 142 around the y axis results in no movement of the output inner universal 137B. However, rotation of output shaft 142 around the y ax is results in movement around the y axis of the output outer universal 136B.

The outer housing 139 is rotatably coupled to the middle housing 140 via a bearing assembly (not shown). The middle housing 140 is rotatably coupled to the inner housing 138 via a second bearing assembly (not shown). This enables rotation about the x axis between both the inner housing 138 and the middle housing 140 and the outer housing 139 and the middle housing 140. Thus, middle housing 140 rotates relative to inner housing 138 and outer housing 139.

The bearing assemblies are concentric and are nested inside one another. This concentric configuration allows both bearings to be assembled simultaneously, for easy assembly at any scale. Thus, the rotation of the input shaft 141 is transmitted through the housings and the universals to the output shaft 142 so that bidirectional rotation of the input shaft 141 results in bidirectional rotation of the output shaft 142. An actuator (not shown), which can be located in the forearm 16, rotates the input shaft 141 about the x axis (roll axis).

The linkage assembly 143 provides movement about the y and z axes of the output shaft 142 simultaneously. The linkage assembly 143 includes four links 144a, 144b, 147a, 147b, each having hooked ends (not shown). The links 144a, 144b are pivotally coupled about the y and z axes by a ball socket (not shown) at corresponding link attachments 145a, 145b, via the hooked ends. The link attachments 145a and 145b are rigidly attached to the middle housing 140. The links 147a and 147b are attached in a similar manner to the outer housing 139. Movement of the links 144a, 144b in the general direction of arrows 146 causes rotational movement of the inner housing 138 about the z axis of the wrist 134.

Movement of the links 147a, 147b in the general direction of arrows 146 results in rotational movement of the inner housing 138 about the y axis of the wrist 134. Any displacement of inner housing 138 relative to input shaft 141 is mirrored on output shaft 142 relative to inner housing 138. Hence, there is a 2:1 amplification of movement of output shaft 142 over inner housing 138. This enables a full hemisphere of motion.

The links 144a, 144b, 147a, and 147b are confined to move in the x-y plane. Each link 144a, 144b, 147a, 147b is connected to a corresponding linear carriage (not shown). The linear carriages are located within the forearm 16 and are fully symmetrical. Each linear carriage moves the corresponding link attached to it in a back and forth direction as indicated by arrow 146. The linear carriages are coupled and actuated by actuators (not shown) located in the forearm 16 or base. The linear carriages include a 2:1 force multiplier that counteracts a 2:1 force divider inherent to the kinematics of the system. Inclusion of the 2:1 force multiplier increases the stiffness of the wrist 134 by a factor of four. Corresponding linear carriages actuate links 144a and 147a in opposition to links 144b and 147b in order to actuate the z and y axes, respectively. Also, the linkages inherently preload one another, thereby eliminating their source of backlash.

The wrist 134 provides movement about the x, y, and z axes simultaneously. The wrist 134 provides up to 180 degrees of motion about the y and z axes for the output shaft 142. The input shaft 141 is bidirectionally rotatable 360 degrees simultaneous with movement about the y and z axes. Thus, the work envelope of the wrist is a full hemisphere of motion.

An end cap 148 guides and positions the input shaft 141 and links 144a, 144b, 147a, 147b within the forearm 16. The input shaft 141 can be rotated inside the forearm within a ring bearing (not shown). The input shaft 141 can be coupled to a pulley assembly (not shown) within the forearm 16. This pulley assembly can be coupled to an actuator (not shown) located either within the forearm 16 or in the actuator base of FIG. 1. The actuator would transmit movement to the pulley assembly in order to move the input shaft 141.

The output shaft 142 has an end effector 149 for holding all types of tools (not shown). Circuitry can be routed through the arm to provide power to tools coupled to the end effector 149 that require electrical or pneumatic power. Also, the tendon or cable-driven arrangement (in accordance with the antibacklash scheme described below in detail) negates backlash in two of the three axes. In addition, the wrist 134 of the present invention has low stiction, high stiffness, and high strength-to-weight ratio.

For microsurgical applications, the wrist 134 can be approximately one inch in diameter, weigh approximately three ounces, and have a payload of about three inch-pounds. This allows the wrist 134 of the present invention to sustain a high work volume, while being lightweight, compact, and miniature in size.

Alternatively, in a preferred embodiment, the wrist 134 of FIG. 11 is modified to exclude components 136a, 136b, and 137b. Also, output shaft 142 is rigidly attached to housing 138 so that output shaft 142 cannot move relative to housing 138. In other words, output shaft 142 could be excluded and housing 138 extended so that housing 138 essentially becomes the output shaft.

By excluding the above mentioned components, the wrist 134 is transformed into a standard universal joint with dual bearing rings attached to the pitch and yaw actuation links. This arrangement provides decoupling of the pitch and yaw axes and allows the preferred wrist to have zero backlash in all axes. In addition, elimination of the aforementioned components provides zero backlash in the pitch, yaw, and roll axes and also provides greater efficiency, thereby reducing friction. Also, elimination of the aforementioned components reduces the work volume of the master robot by half.

Similar to the wrist 134 discussed above, the actuation links of the preferred wrist are activated by the tendons, which are passed through the elbow and shoulder joints to the base. Likewise, the roll is activated by tendons which rotate the universal joint, passing rolling motion to a face plate located at the end of the wrist. The face plate allows for attachment of various components, such as variations of the stylus 13 shown in FIG. 1, depending on the application. Also, similar to the tendons controlling the pitch and yaw axes, the tendons controlling the roll axis pass through the elbow and shoulder joints, and exit the base housing.

Antibacklash Mechanism

Figures 12A, 12B:
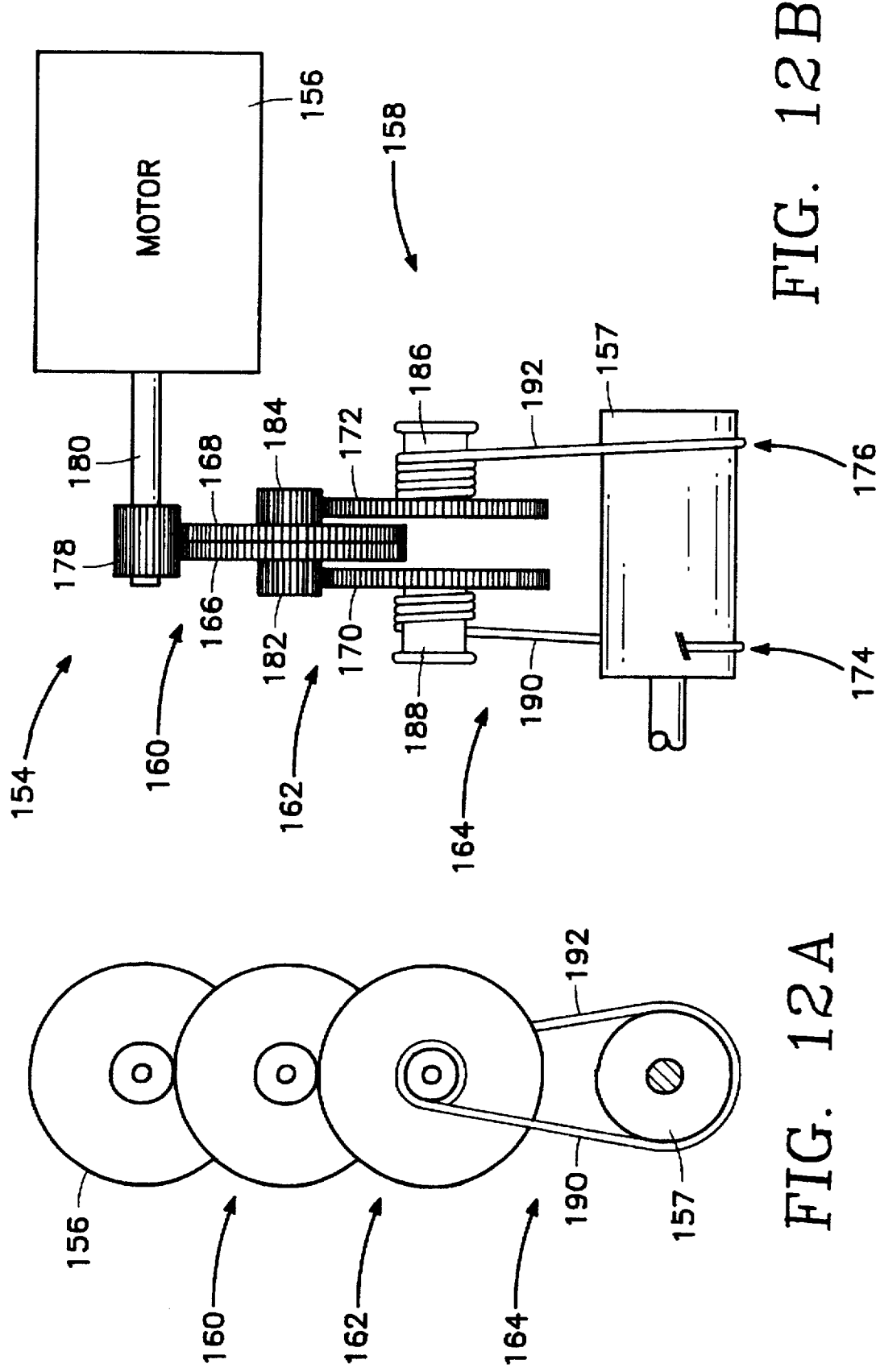
FIG. 12A illustrates a side view of one antibacklash mechanism that can be used in accordance with the present invention.
FIG. 12B illustrates a front view of one antibacklash mechanism that can be used in accordance with the present invention.

FIGS. 12A and 12B illustrate the preferred antibacklash mechanism of the slave robot 8' of FIG. 1B. The input device or master robot 8 of FIG. 1A utilizes a standard single stage antibacklash mechanism. Alternatively, the antibacklash mechanism of the FIGS. 12A and 12B can be used in the master robot 8.

Referring to FIGS. 12A and 12B, the antibacklash mechanism 154 are used with the joints of FIGS. 2–11 to overcome the problems of conventional antibacklash schemes. The antibacklash mechanism is incorporated in the respective robots 8, 8' between the actuators, such as motors 156 at the actuator base, and an output 157 or the device to be actuated, such as the output link 62 of FIG. 5 of a particular joint.

The antibacklash mechanism 154 is a multiple stage device not limited to any particular number of stages. The antibacklash mechanism 154 utilizes a drivetrain system 158 with drive components such as gears, belts, and/or cables. FIGS. 12A and 12B illustrate the antibacklash mechanism 154 having three stages 160, 162, and 164 with a pair of gears 166 and 168 and 170 and 172 at the first 160 and second stages 162, respectively.

Two independent transmission paths, defined by the gears 166, 182, 170, and 168, 184, 172, are formed as two identical geartrains in parallel for each drive. For example, a given joint's motor 156 would have one spur pinion 178 on its shaft 180 which would engage with two independent gears 166 and 168 of the first stage 160. The two independent transmission paths are mechanically coupled only at an input, such as the motor 156, and an output, such as an actuation pulley located on a particular joint.

The first and second stage gears 166 and 168 are free to rotate independent of each other, respectively. The pinion 178 on the motor 156 at the input drives both of the independent first stage gears 166 and 168 to complete a first stage 160 reduction. Two second stage 162 pinions 182 and 184 are rigidly attached to each of the first stage gears 166 and 168, for example on a gear shaft. The two second stage 162 pinions 182 and 184 drive the two independent second stage gears 170 and 172, thus completing the second stage 162 reduction (additional gear stages can be used).

Each of the second stage gears 170 and 172 drives an independent actuation drum or tendon spool 186 and 188 on a common shaft. Two cables 190 and 192, each attached to one of the spools 188 and 186, terminate on the output, which can be for example the actuation pulleys 106 and 108 of FIGS. 4-11. The cables 190 and 192 actuate the particular joint, thereby completing the third stage 164 and completing a dual drive system 174 and 176. Thus, with this arrangement, the only common points between the dual drive system 174 and 176 are at an origination at the input 156 (i.e. the motor 156) and the termination at the output 157 (i.e. the actuation pulleys 106 and 108 at the joint).

This dual drive arrangement allows for cable tensioning, eliminates backlash, and maximizes mechanical efficiency. Hence, from this feature, one of the advantages of the antibacklash mechanism of the present invention is convenient preloading of the gear stages 160, 162, and 164 to eliminate backlash. The dual drivetrain system is preloaded by first disengaging the motor 156 from the first stage 160 gears 166 and 168 so that the two gears 166 and 168 can be counter-rotated relative to one another. This counter-relation preloads the cables 190 and 192 to the desired tension. This rotation passes from stage to stage until all the cables become tensioned. When the desired preload tension is achieved, the motor 156 is simply re-engaged and the preload is locked.

Also, by disengaging the motor 156, the two drivetrains 174 and 176 can be reloaded relative to one another if necessary. In addition, since the preload is passed from one stage to the next stage, the value of the preload is proportional to any gear ratios between the stages 160, 162, and 164. Moreover, an optimum preload is achieved automatically in all the stages 160, 162, and 164 simultaneously because the preloading is passed via the gearing from the input motor 156 to the output 157. This preload is transmitted throughout the entire dual drivetrains 174 and 176, thereby eliminating backlash in all drivetrains. Further, the preload is transmitted proportionately to the gear ratio for each stage, to optimize the preload for maximum mechanical efficiency, unlike the prior art where each stage is independently preloaded.

Thus, the antibacklash mechanism 154 of the present invention provides geartrains with zero backlash, convenient preload adjustment, preload adjustment of all stages simultaneously, and stage preload proportional to stage ratio to achieve maximum mechanical efficiency. Also, since the required gear ratio for the microsurgical robot manipulator described above is between the actuator and each joint, the antibacklash mechanism of FIGS. 12A and 12B is global for all the joints and encompasses a wide range of ratios. In addition, for the cable-driven robot manipulator, the cable preload is adjustable to accommodate stretching over time.

Detailed Components of the Microsurgical Robot Manipulator

Figure 13:
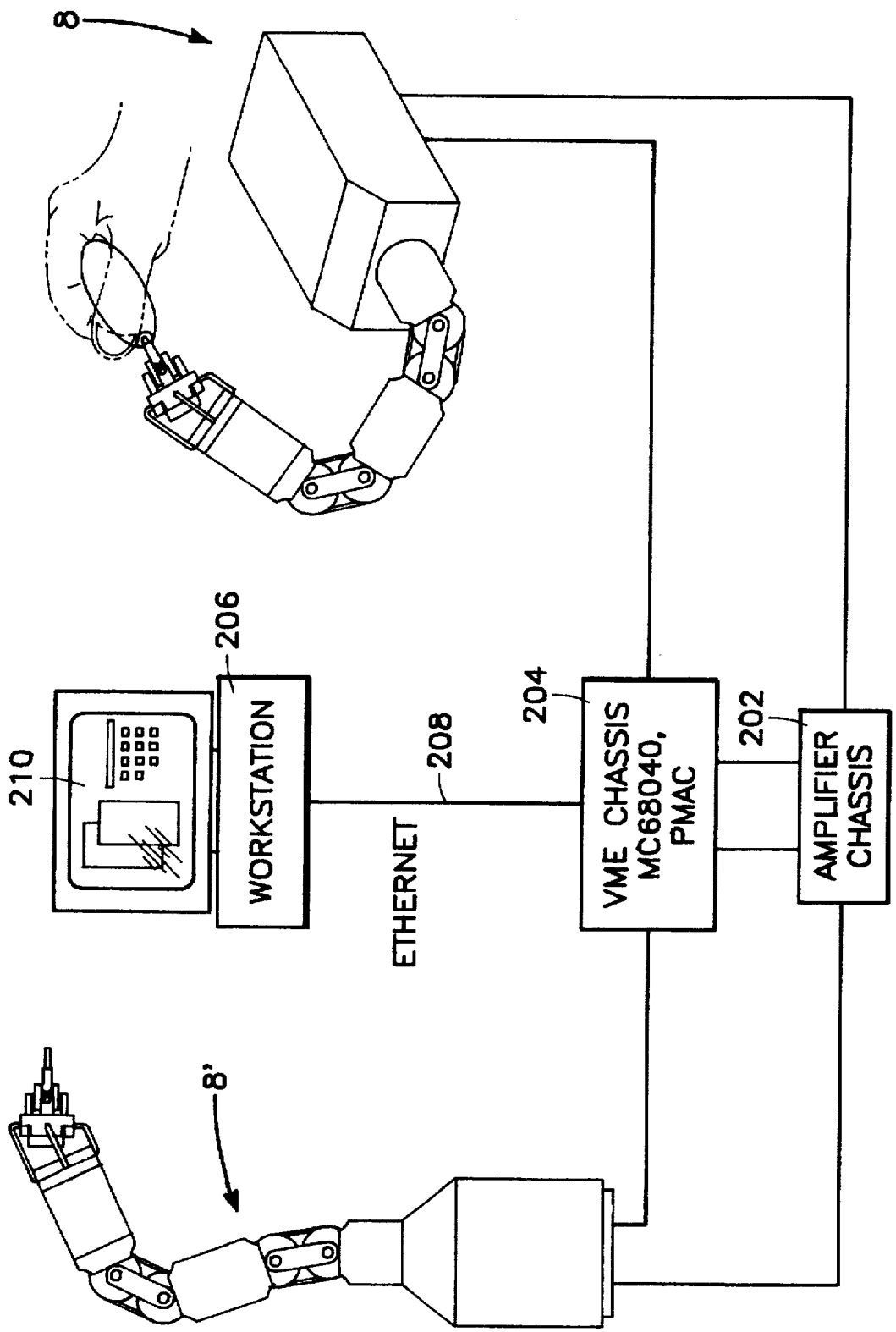
FIG. 13 illustrates an overview of the interaction between the sub-systems of the robot system of the present invention.

FIG. 13 illustrates an overview of the interaction between the sub-systems of the robot system of the present invention. The input device 8 functions as a master robot in a microsurgical teleoperated robot system. The overall system architecture includes a slave robot manipulator 8' coupled to an amplifier chassis 202. The amplifier chassis 202 is coupled to a control chassis 204, such as a VME chassis, which is coupled to a workstation 206, such as a UNIX workstation via standard twisted pair Ethernet 208. The workstation has a graphical user interface 210 which can have a keyboard or other input device for ease of control by a user. Also, the amplifier chassis 202 is coupled to the motors of the master robot manipulator 8 and the control chassis 204 is coupled to the encoders of the master robot manipulator 8.

A force feedback can be applied to the input device 8 and can be generated from the slave robot 8'. This would enable a user to operate the slave robot 8' via the input device 8 without physically viewing the slave robot 8'. Also, the force feedback can be generated from the workstation to represent fictitious forces. These fictitious forces are very desirable because they can constrain the input device's 8 control of the slave robot 8' to be within imaginary predetermined boundaries.

Components of the robot system are categorized into four sub-systems. The subsystems include the mechanical sub-system, the electronics sub-system, the servo-control sub-system, and the high-level software control sub-system. These sub-systems are described in detail in sections that follow.

Mechanical Sub-system:

Internal Components of Master Robot

Figure 14B:
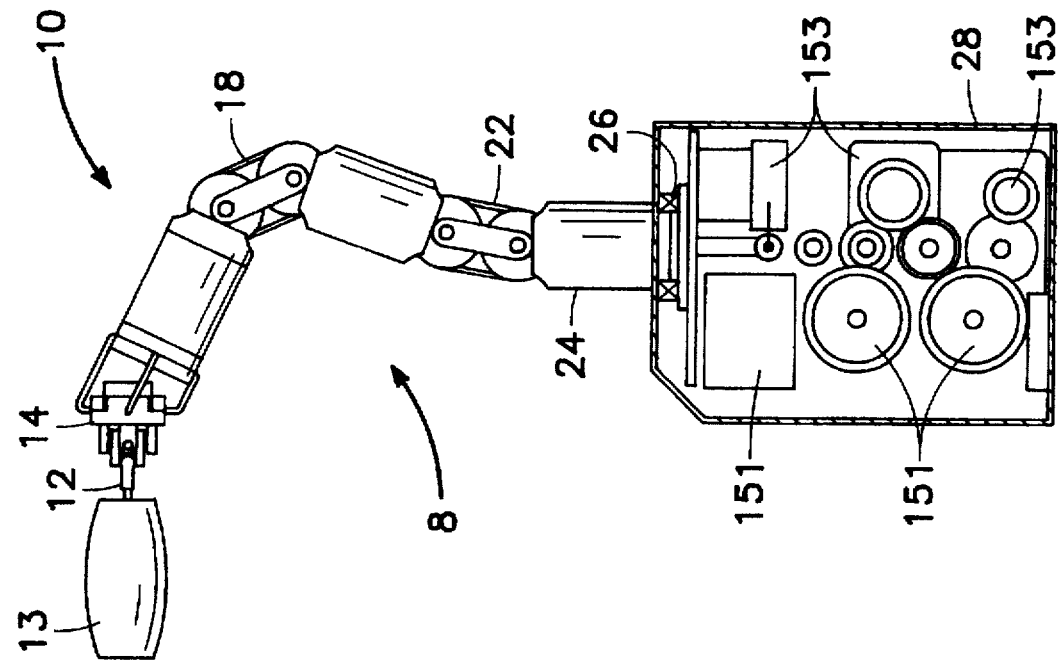
FIG. 14B illustrates a left side cut-away view of the base of the master robot of the present invention.
Figure 14A:
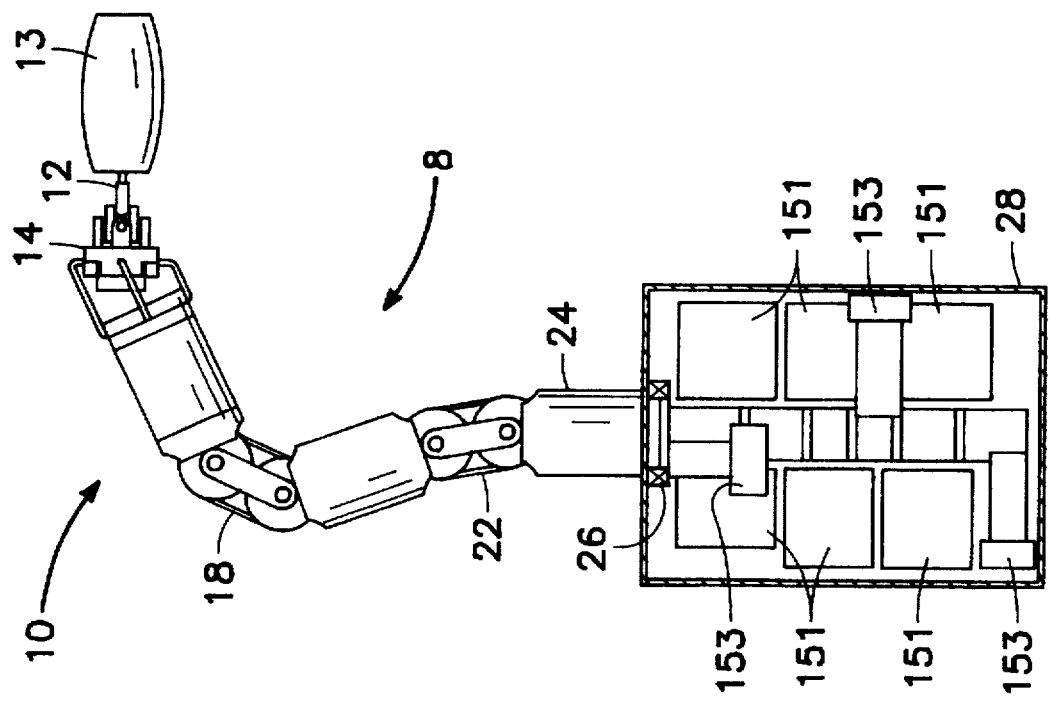
FIG. 14A illustrates a front cut-away view of the base of the master robot of the present invention.

FIG. 14A illustrates a front cut-away view of the base of the master robot of the present invention and FIG. 14B illustrates a left side cut-away view of the base of the master robot of the present invention. The base 28 houses components that control the arm. The arm 10 is mounted to the actuator base 28 which can be a cylindrical base housing.

For microsurgical applications, the base housing is preferably about 23 cm long, 18 cm wide, and 10 cm high. The tendons passing through the arm 10 of FIGS. 4-8 enter the base 28 through a connection between the arm 10 and the base 28. The tendons are wound on five independent tendon spools (not shown), one for each axis (the shoulder 22 axis, the elbow 18 axis, and the pitch, yaw, and roll axes of the wrist 14). The torso 26 rotates relative to the base 28 about a sixth axis and is driven by gears (not shown).

In order to decouple the five axes from the sixth axis (torso), the tendons of the other five axes are twisted about their length along the sixth axis. Although this arrangement of the present invention produces decoupling, it does vary the tension in the tendons by a small percentage (<1%). Also, as a result, travel of the sixth axis is restricted to approximately 30 degrees. However, since the input device 8 has indexing capabilities, a high range of motion is not necessary.

Each of the six axes is equipped with a high-resolution optical encoder 151 (for a total of six encoders), such as an encoder capable of 40,000 counts per revolution. The six encoders 151 are housed in the base 28 and are necessary for reducing the amount of gearing necessary to achieve the required positional resolution while limiting friction.

The encoders 151 are attached to the tendon spools and the torso axis via a standard single stage antibacklash geartrain. Alternatively, the antibacklash geartrain described in FIGS. 12A and 12B may be utilized. In the preferred embodiment, geartrain ratios vary from about 1.25:1 on the torso 26, shoulder 22, and elbow joints 18 to as high as about 5.3:1 on the roll axis.

In addition, the base 28 also preferably includes three arm motors 153 and three wrist motors (not shown) to create the force-feedback capability on the torso 26, shoulder 22, and elbow axes 18, and the three-axis wrist 14, respectively. The motors preferably have Hall effect sensors incorporated within. The force feedback can be applied to the input device 8 for providing feedback to an operator of the input device 8. The force feedback can be generated from the slave robot 8' (see FIG. 1B) which the input device 8 controls. Also, the force feedback can be generated from an external device, such as a programmed processor, to produce fictitious forces on the input device. The fictitious forces can represent desired boundaries to constrain the slave robot 8' of FIG. 1B within.

With the aforementioned arrangement, the input device 8 can produce approximately six ounces of force, and may be driven to produce approximately 13 Newtons force and about 300 N-mm of torque at the wrist. Minimizing the force output minimizes the friction and reflected inertia for a given motor. The motors are preferably DC brushless motors, but could be replaced with any other type of motor. These motors are attached to the tendon spools via a standard single stage spur geartrain. Also included in the base 28 is the electrical wiring (not shown) to support the motors and encoders 151, all of which are connected to electrical connectors (not shown) at the rear of the housing for electrical interface with an external source (not shown).

Thus, the input device 8 has 6-axes of positional input with the capacity to produce 6-axes force-feedback. The drive motors create the force-feedback capability on the torso 26, shoulder 22, and elbow 18 axes. Also, the plurality of high-resolution optical encoders 151 reduce the amount of gearing necessary to achieve the required positional resolution while limiting friction.

The total work volume of the input device 8 is determined by the independent joint limits described above, primarily constrained by that of the torso 26 (with the aforementioned arrangement, the torso has a range of motion of approximately 30 degrees). This results in a wedge-shaped work volume, with the apex aligned with the torso axis. The positional accuracy is maintained over the entire volume.

In summary, with the aforementioned arrangement, very low inertia, very low frictional aspects, and zero backlash in the axes of the wrist of the master robot 8 are achieved. In addition, since the master robot 8 has indexing capabilities, a high range of motion is not necessary, as required in the slave robot 8'.

Internal Components of Slave Robot

Figure 14D:
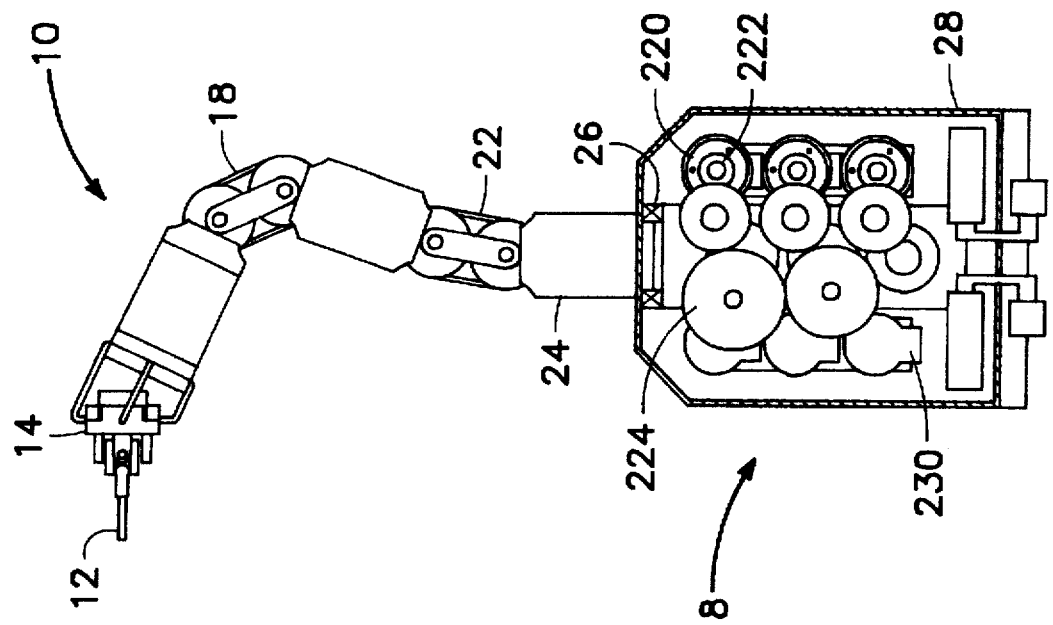
FIG. 14D illustrates a right side cut-away view of the base of the slave robot of the present invention.
Figure 14C:
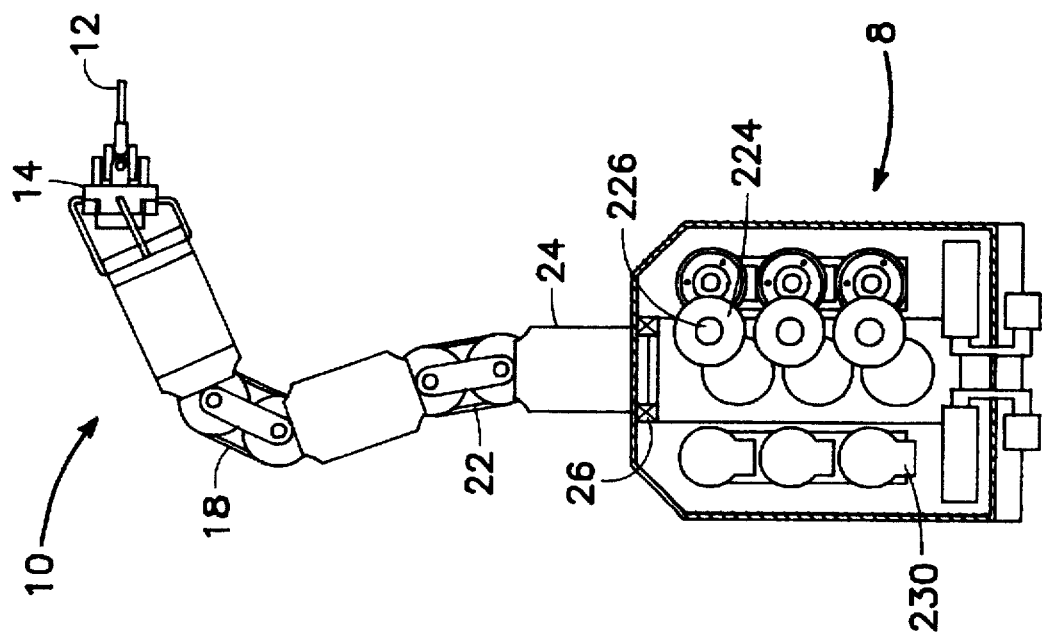
FIG. 14C illustrates a left side cut-away view of the base of the slave robot of the present invention.

FIG. 14C illustrates a left side cut-away view of the base of the slave robot of the present invention and FIG. 14D illustrates a right side cut-away view of the base of the slave robot of the present invention. The base 28' of the slave robot 8' houses motors 220' with shafts 222', encoders (not shown), gears 224', pinions 226', bearings (not shown), cable spools (not shown) and other conventional components. The motors preferably have Hall effect sensors incorporated within. The arm 10' of the slave robot 8' has tendons or cables, pulleys, and linkages located in the arm 10' and joints 14', 18', and 22' of the slave robot 8'. These components mechanically operate the end effector 12' of the slave robot 8' under control of the master robot 8 of FIG. 1A.

The slave robot 8' is preferably a compact six degree of freedom tendon-driven robot having very precise relative positioning capability (down to 10 microns) as well as a very high work volume. Physically, the arm 10' measures 2.5cm. in diameter and is 24.6 cm long from the actuator base 28' to a tip of the end effector 12'. The arm 10' is mounted to the actuator base 28' which can be a cylindrical base housing measuring 12.0 cm in diameter by 18.0 cm long. Also, the double-jointed decoupled cable or tendon-driven joints described in FIGS. 4–10 are used in the slave robot 8'. As shown in FIGS. 4–10, the joints 18' and 22' have very high ranges of motion, are double-jointed, and can pass any number of tendons through which are completely mechanically decoupled from the particular joint's motion.

Each degree of freedom of the robot is actuated by its own motor, such as a D.C. brushless motor encapsulated inside a sterile housing. Thus, there are six motors 220'(six degrees of freedom), three for the slave wrist joint 14', one for elbow joint 18', one for the shoulder joint 22', and one for the torso joint 26', which rotates the shoulder 24' about the actuator 28' or torso. The motors 220' are coupled to the gears 224' directly or via the pinions 226' for operating the gears 224'. Preferably, the gears 224' and pinions 226' are spur gears to define spur drivetrains. Although the number of gears 224' and pinions 226' to be used can vary with different design considerations, motor 220', pinion 226', and gear 224' configurations of the present invention are preferably in accordance with the novel antibacklash system described above in detail in FIGS. 12A and 12B.

Each motor 220' is equipped with an optical encoder (not shown) on its shaft 222' for position sensing. The optical encoders preferably have 512 lines per revolution and produce outputs of 2048 counts per revolution. Since the smallest incremental movement during microsurgery is approximately 10 microns, 10 encoder counts is the minimum desirable incremental movement. As a result, one encoder count corresponds to one micron movement at the tip of the end effector 12'. Based on the above dimensions and geometry of the preferred slave robot arm 10', the minimum required gear ratio for the slave wrist joint 14' is approximately 60:1, 300:1 for the elbow joint 18', and approximately 550:1 for both the torso 26' and shoulder 22'joints.

The gear reduction of the slave robot 8' based on the tendons for each joint can be accomplished as described above in FIGS. 4–8. Preferably, the gear reduction is approximately 2.5:1 in the torso joint 26', wrist pitch, and wrist yaw axes (see FIG. 11), and approximately 1.5:1 in the shoulder 22' and elbow 18' joints, and the wrist roll axes (see FIG. 11). In addition, the slave robot 8' has multi-stage spur drivetrain gear reductions based on the multi-stage gearing arrangement in the antibacklash scheme of FIGS. 12A and 12B described above in detail.

The slave wrist pitch, yaw, and roll axes all have two-stage spur reductions of approximately 37:1, making the total reduction ratios approximately 92:1 (2.5 tendon gear reduction multiplied by 37 multi-stage gear reduction) for the wrist pitch and wrist yaw axes and approximately 60:1 (1.5 tendon gear reduction multiplied by 37 multi-stage gear reduction) for the roll axis. Also, the torso 26' and elbow 18' joints of the slave robot 8' all have three-stage spur reductions of about 269:1, whereas the shoulder joint 22' has a three-stage reduction of about 411:1. The resulting total reduction ratios for the slave robot 8' are approximately 667:1, 614:1, and 370:1 for the torso 26', shoulder 22', and elbow joints 18', respectively.

The microsurgical slave robot 8' of the present invention can be autoclaved for sterilization. Since the motors 220' and optical encoders are not capable of surviving such an environment, these components are removably attached within the actuator base 28'. The motors 220' and optical encoders can be removed prior to sterilization and reinstalled afterwards. The motors 220' are removably attached on two mounting blocks 230' within the actuator base 28' on alignment pins (not shown). Each mounting block 230' contains three motors. The motors 220' are coupled to an electrical power source (not shown) via an electrical connector (not shown). The housing of the actuator base 28' tightly encloses the base 28' with screw mounts (not shown) or quick-release latches (not shown).

The slave joints 14', 18', and 22' of the microsurgical slave robot 8' require high stiffness. Thus, relatively larger diameter tendon cables with short path lengths are used as described in FIGS. 4-8 above. Also, low stiction (stick/slip characteristic) is needed to achieve precise motions, especially since the optical encoder position sensors are in the slave robot's 8' base 28'. Low stiction is accomplished by using precision ball bearings (not shown) in every rotating location, such as in all of the pulleys, joint axes, and drive shafts, to eliminate metal-to-metal sliding contact.

The arm 10' has a large work volume so that the actuator base 28' will not have to be repositioned frequently during tasks. For example, the torso joint 26' is capable of rotating the shoulder 24' 360 degrees of full rotary motion about the y axis. The elbow joint 18' and the shoulder joint 22' are capable of 360 degree limited rotary motion about the z axis. The wrist joint 14' is capable of motion about the x, y, and z axes (as described in FIG. 11 above). Since each axis is completely decoupled from the joint's motion, the wrist joint 14' is capable of 180 degrees motion about the y and z axes (pitch-and-yaw motion) and 540 degrees of continuous motion about the x axis (roll motion) and thus, operates in a full hemisphere of motion.

Figure 15:
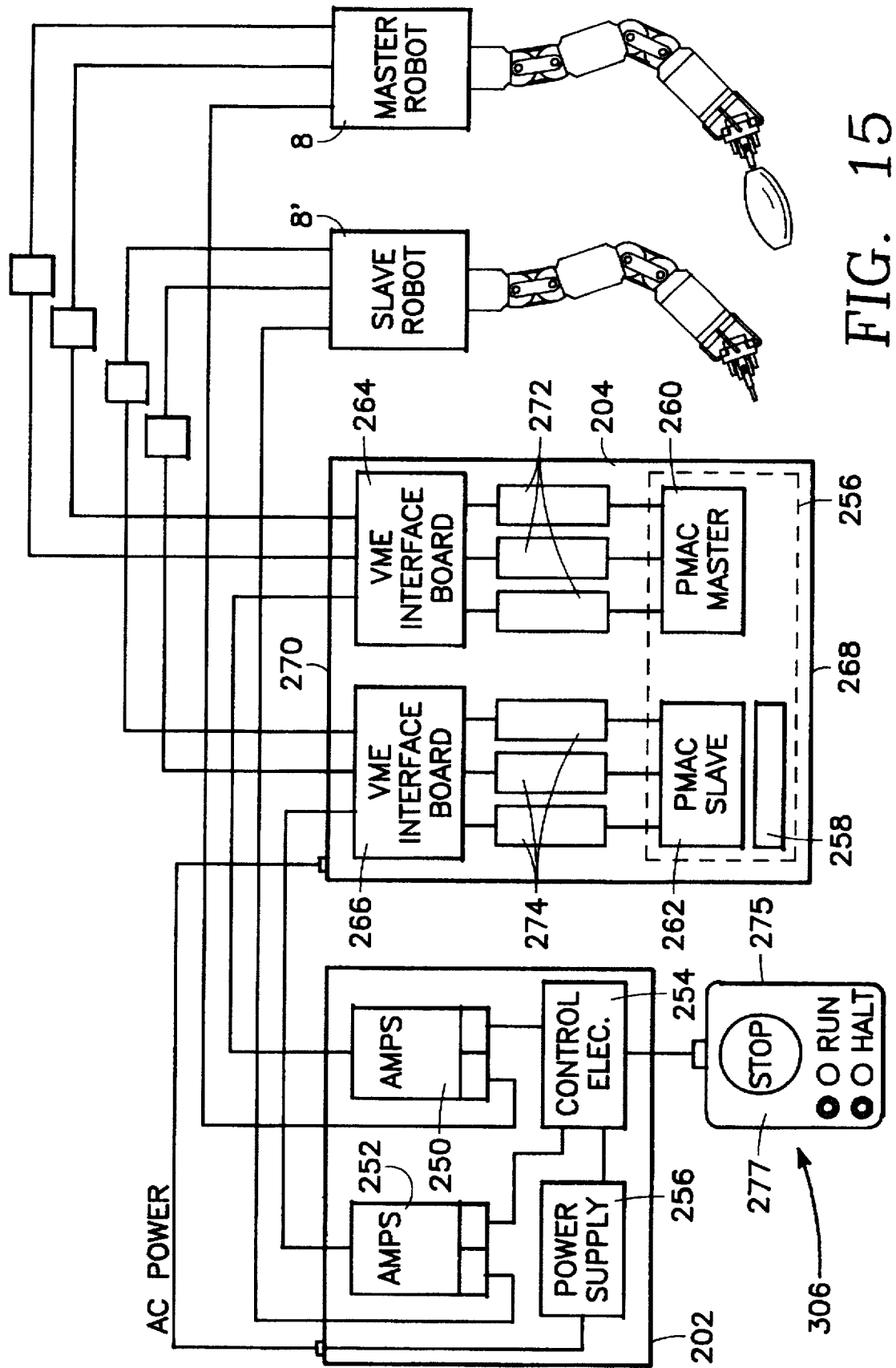
FIG. 15 is a block diagram illustrating the interconnections of the master and slave robots with the amplifier chassis and the control chassis and their respective components.

Servo-control Sub-systems:

FIG. 15 is a block diagram illustrating the interconnections of the master and slave robots with the amplifier chassis and the control chassis and their respective components of the servo-control sub-system. The amplifier chassis 202 can contain, for example, slave robot motor drive amplifiers 250 for each corresponding motor of the slave robot 8', master robot motor drive amplifiers 252 for each corresponding motor of the master robot 8, a system control electronics board 254, and an amplifier power supply 256.

The amplifier chassis 202 is coupled to the VME chassis 204 (with for example, analog inputs and control signals), the slave robot 8' (with for example, motor drive signals), the master robot 8 (with for example, motor drive signals) and to an electronics sub-system 306, as shown in below in FIG. 16. The electronics sub-system 306 comprises control electronics 275 and controls typical commands such as panic stop, run, and initialize. These commands can be monitored with a control panel 277 with visual indicators, such as light emitting diode (led) indicators. The electronics sub-system will be discussed in detail below. The amplifier chassis' 202 main power is provided by the VME chassis 204 and is preferably alternating current (AC).

Individual amplifiers 250, 252 are preferably secured to the amplifier chassis 202. This provides a thermal path to the amplifier chassis 202 and also provides a favorable orientation with respect to the amplifier chassis' 202 air flow pattern to allow individual amplifiers 250, 252 to run cool. A frame (not shown) of the amplifier chassis 202 contains all necessary amplifier interface wiring. This allows the amplifier chassis 202 to be highly modular and to facilitate rapid check-out and trouble-shooting. The control electronics board 254 has a braking function for holding the motors in place when they are not under control of the amplifier chassis 202.

The VME chassis 204 can be comprised of many suitable configurations capable of performing the above. For example, the VME chassis 204 can house a VME backplane 256 with two Motorola MVME-167 computer boards 258, Proc0 and Proc1, for high level system control, master and slave servo control boards 260, 262, such as Delta Tau Data Systems, Inc.'s PMAC boards, and power supplies (not shown). The PMAC boards preferably receive two channel quadrature outputs from the encoders of the master and slave robots 8, 8', respectively. Also, the PMAC boards preferably receive backup motor position information from the Hall effect sensors built into the motors of the master and slave robots 8, 8', respectively.

Proc0 performs kinematic, communication and high-level control functions. Calls to subroutines that read and set joint angle positions of the robot are made from the high-level real-time software on Proc0. These routines, through shared memory implemented between Proc0 and Proc1, provide setpoints and read current joint angles of the robot. Proc1, in turn, passes the setpoints for controlling the robot to the servo control board and retrieves the joint angles measured by the servo-control board.

The VME chassis 204 also can include supporting master and slave interface boards 264, 266, front and rear panels 268, 270, and master and slave input/output blocks 272, 274. The front panel 268 can have a main power control (not shown) provided by alternating current (AC) and the rear panel 270 can control communication access with the workstation 206. The PMAC servo boards 260, 262 can generate two phase drive signals for sinusoidal commutation of the systems brushless DC motors. The PMAC boards 260, 262 receive optical encoder feedback from the motor shafts and provides low level control of the motors. The input/output blocks 272, 274 and interface boards 264, 266 can control signal and power distribution to the rear panel 270 of the VME chassis 204.

The servo-control sub-system provides digital sine-wave commutation, automatic trajectory generation, shared memory interface, built-in amplifier/encoder interface, and robust closed loop control.

Figure 16:
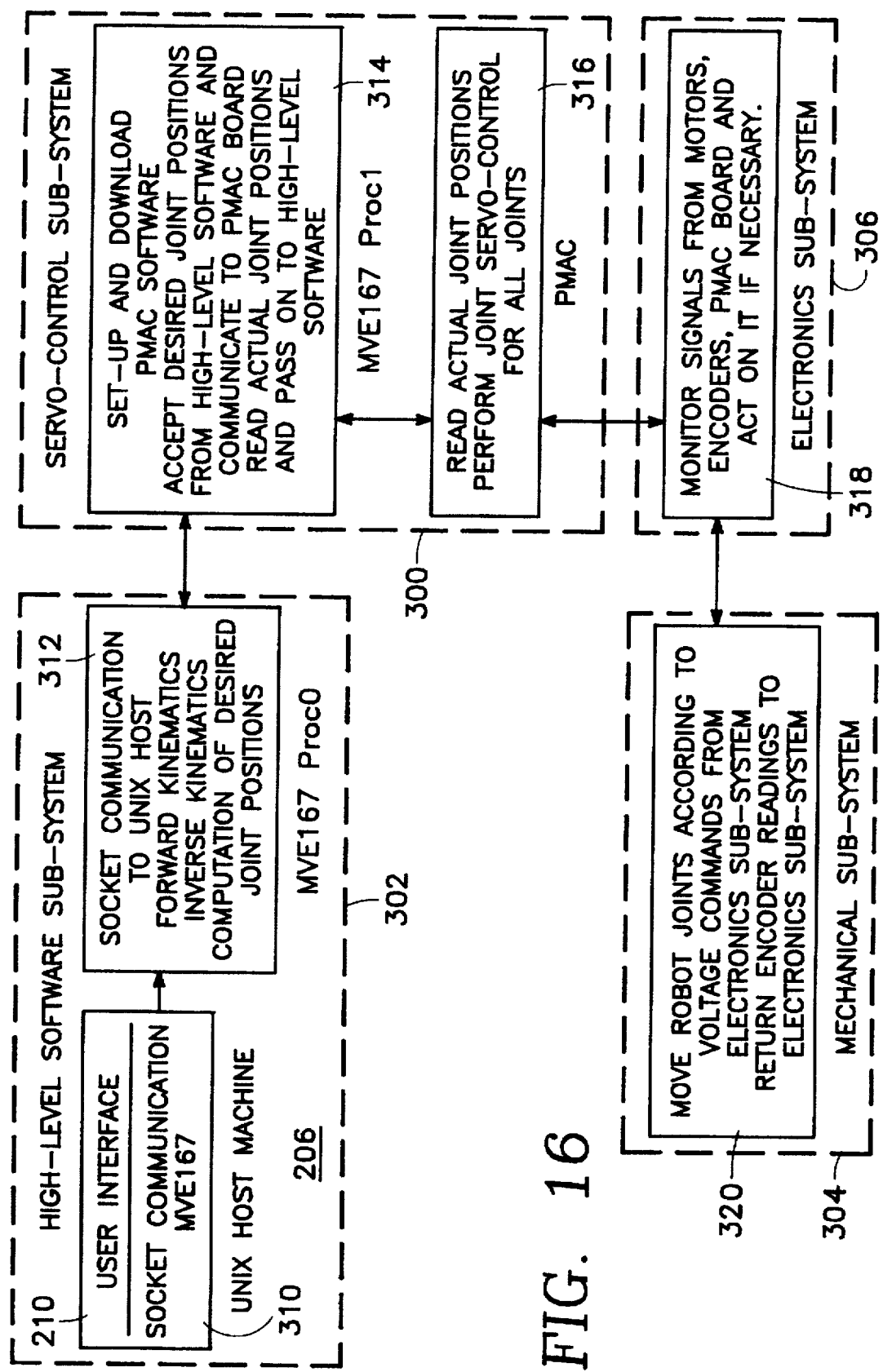
FIG. 16 is a block diagram illustrating the interaction of the servo-control sub-system and the high-level software sub-system with the mechanical sub-system and the electronics sub-system of the present invention.

Interaction of Sub-systems:

FIG. 16 is a block diagram illustrating the interaction of a servo-control sub-system 300 and a high-level software sub-system 302 with a mechanical sub-system 304 and an electronics sub-system 306 of the present invention. The servo-control sub-system 300 is partly hardware and partly software. Referring to FIG. 16 along with FIGS. 15 and 13, the relevant hardware components of the servo-control sub-system are amplifier cards within the amplifier chassis 202 and the controller boards on the VME chassis 204.

Software runs under an operating environment, such as VxWorks operating environment, on the MVME167 boards of the VME chassis 204 to perform certain functions. These functions include setting-up control parameters and running a servo-loop on the PMAC boards, to control the six motors 220, implementing communication between the MVME167 and PMAC boards, initializing the servo-control system and communicating with the electronics sub-system, and communicating with a high-level software sub-system. The high-level software sub-system resides on the UNIX workstation 206 and on the Proc0 board on the VME chassis 204.

The high-level software sub-system 302 is connected to the user interface 210 and controls initialization of the software and hardware. Also, a communication system 310, which can be based on the UNIX socket protocol or Real-time Innovation, Inc.'s Network Data Delivery System (NDDS), connects the UNIX host to Proc0. This high-level software sub-system 302 implements a number of demonstration modes 312 of robot control and computes forward and inverse kinematics and desired joint positions.

A first servo-control software module 314 is implemented on Proc1, is coupled to the high-level software through the backplane of the VME chassis with the use of shared memory between Proc0 and Proc1. The first module 314 configures and downloads PMAC software, accepts the desired joint positions from the high-level software and communicates these positions to the PMAC boards, and reads the actual joint positions and sends these positions to the high-level software. Also, a second module 316 of the servo-control sub-system performs joint servo-control for all the joints based on the reading of the actual joint positions.

The electronics sub-system 306 is coupled to the servo-control sub-system 300 and will be discussed below. The mechanical sub-system 304 is coupled to the electronics sub-system 306 and has a mode 320 which moves robot joints according to voltage commands from the electronics sub-system and returns encoder readings to the electronics sub-system.

Figure 17:
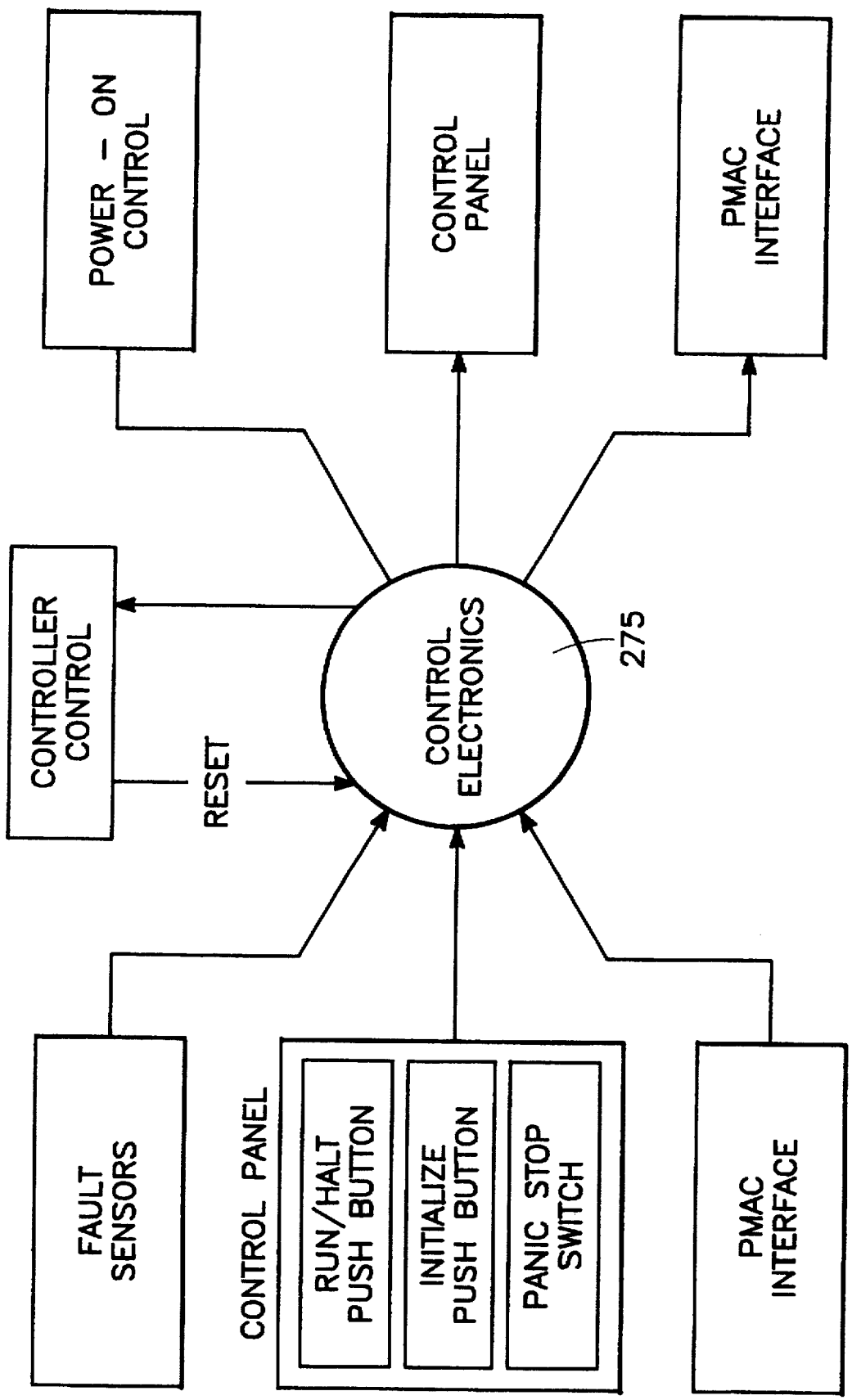
FIG. 17 is a block diagram illustrating a sample functional interface of the electronics sub-system with the mechanical and servo-control sub-systems.

Electronics Sub-system:

FIG. 17 is a block diagram illustrating a sample functional interface of the electronics sub-system with the mechanical and servo-control sub-systems. The electronics sub-system incorporates sophisticated control electronics 275 to provide control of the power to the motors/amplifiers during power up and power down events.

Figure 18:
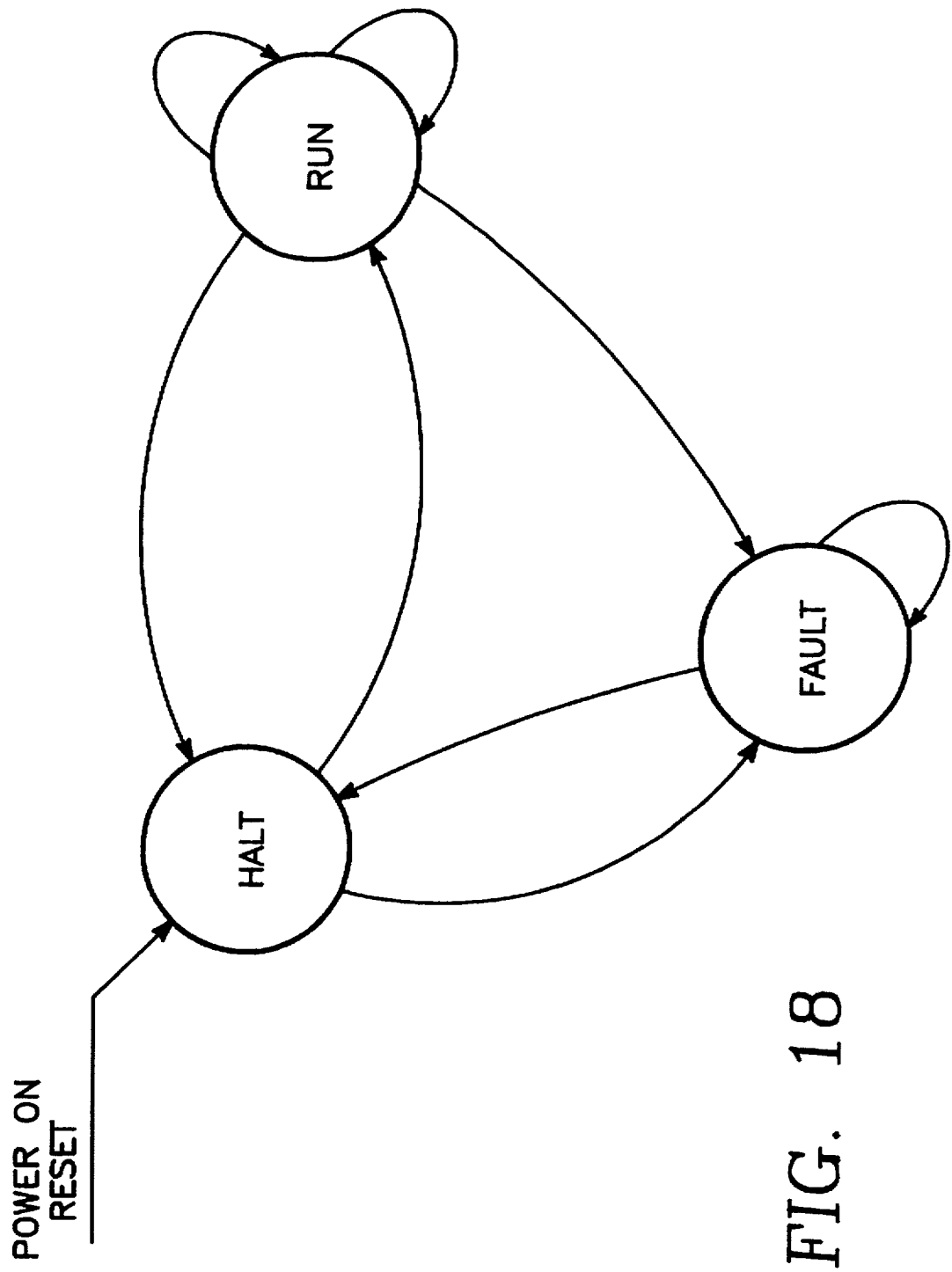
FIG. 18 is a state diagram illustrating sample transitions of the control electronics of the electronics sub-system of FIG. 17.

FIG. 18 is a state diagram illustrating sample transitions of the control electronics of the electronics sub-system of FIG. 17. After power on, the system can halt, fault, or run, depending on the circumstances. The transitions between the conditions are shown in FIG. 18. The control panel 277 provides remote access to switches and indications needed to operate the robot system. For instance, the control panel 277 can have a PANIC STOP switch to halt operation quickly. Also, the control electronics 275 requires inputs from an operator in order to apply power to the motor amplifiers. Further, indicators, such as, RUN and FAULT led indicators show the current status of the control electronics 275.

Example Operation:

For example, referring to FIG. 17 along with FIG. 18, initially, an operator turns on AC power (or resets the power) from the VME chassis 204 in order to power the VME chassis 204 and the power supply 256 in the amplifier chassis 202. This also provides power to the control electronics 275. During this step, the motors of the master and slave robots 8, 8' are held in a brakes-on condition. The RUN led indicator of the control panel 277 is in an off position and the FAULT led indicator is in an on position.

Next, the operator can attempt to enable the motor drive by pressing and releasing an INITIALIZE switch. The FAULT led indicator will either turn off, indicating no faults, or stay on, indicating that a fault condition exists. If the FAULT led indicator turns off, then the operator can press and release a RUN switch (the RUN led indicator led turns on) to start a power up sequence. At this point, the robot is ready for computer control.

The sequence of events leading up to a running system are as follows: First, the control logic monitors two high priority inputs constantly, a PANIC STOP switch and a PMAC heartbeat signal. The PANIC STOP switch is the operator kill button to freeze motion of the slave robot 8' if an error is observed. The PMAC heartbeat signal is a low frequency, preferably 10 Hz, step signal sent by the PMAC boards to the control electronics 275. The signal will not step if failures of the PMAC or MVME-167 boards occur. If the PANIC STOP switch is not in the closed position then a fault is recognized. If the PMAC heartbeat signal is not received then a fault is recognized. In a fault condition the FAULT led turns on and a fault signal is sent to the PMAC servo board. If the system is running, it will stop and brake.

Second, a request to run is initiated when the operator presses and releases the RUN switch on the control panel 277. Upon receiving a run request the control electronics 275 releases the brakes. If one or more of the brakes does not engage, then a fault exists, and the sequence is aborted and the FAULT led indicator turns on.

Third, if all of the brakes indicate that they are enabled, the power to the amplifiers will turn on. If the power on and fuse sensor circuits fail then a fault exists, and the sequence is aborted and the FAULT led indicator turns on.

Fourth, if the sequence is successful then the motors of the master and slave robots 8, 8' will operate under amplifier control until a fault condition occurs or the operator toggles the RUN switch to disable the motor/amplifier control. In summary, the electronics sub-system 306 provides intelligent control of the main power-up and power-down events and the amplifier power-up and power-down events.

Robot Kinematic Algorithms

The following summarizes the kinematics algorithms for the master and slave manipulators, with particular emphasis on computation of the Jacobian and its inverse. The kinematic computations are for each combined manipulator formed by the wrist, together with the articulated mechanism, consisting of torso, shoulder, and elbow joints, that supports the wrist. In addition to providing the overall manipulator system kinematics, the following provides a kinematic analysis of the slave and master wrists. In particular, velocity transformations are provided, that are necessary to relate the incremental movement in the bail angles of the wrist to the corresponding movement in the universal joints of the wrist.

The present invention uses kinematic algorithms for computation of the forward and inverse kinematics of the robot. Kinematic algorithms are described in U.S. Pat. No. 5,303,384, the disclosure of which is incorporated by reference in its entirety. The forward kinematics computation refers to the determination of the tip position and orientation given known joint angle positions of the robot. The inverse kinematics is the determination of the joint angle positions given a desired tip position and orientation.

Figure 19A:
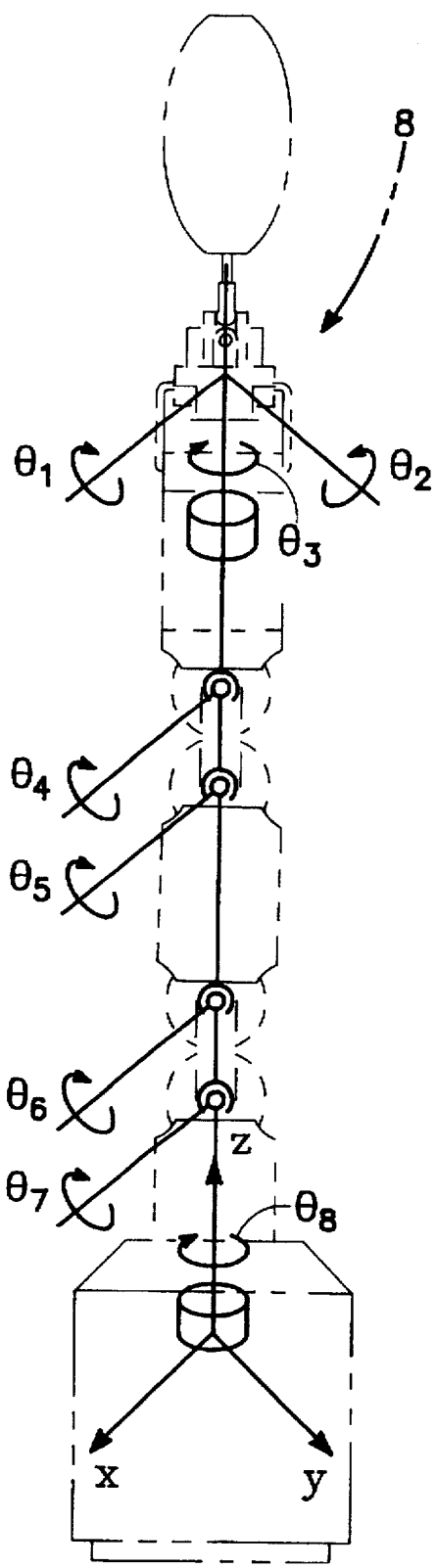
FIG. 19A is a kinematic axes diagram illustrating the kinematics of the master robot.
Figure 19B:
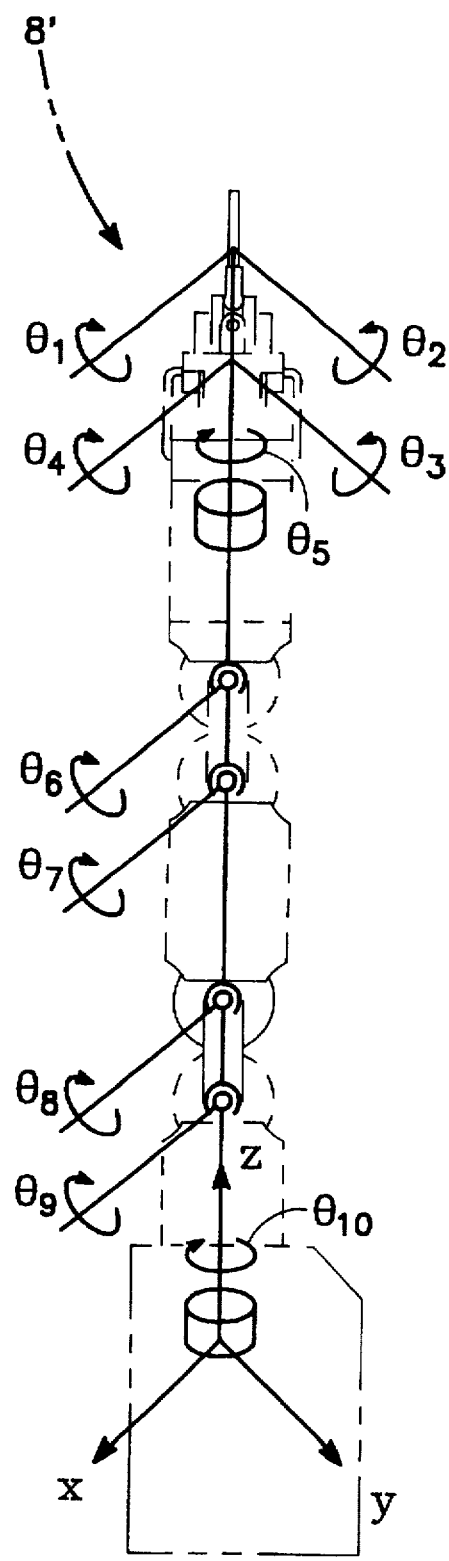
FIG. 19B is a kinematic axes diagram illustrating the kinematics of the slave robot.

Definitions:

FIG. 19A is a kinematic axes diagram illustrating the kinematics of the master robot. FIG. 19B is a kinematic axes diagram illustrating the kinematics of the slave robot. Each angle of each joint is represented by $\theta(k)$. Master Robot: $\theta(8)$ is the roll angle of rotation of the TORSO about an axis perpendicular to the base of the manipulator. $H(8)=[0,0,1,0,0,0]$ is the corresponding axis of rotation. $\theta(7)$ is the pitch angle of rotation of the FIRST SHOULDER JOINT about the pitch axis. $H(7)=[1,0,0,0,0,0]$ is the corresponding axis of rotation. $\theta(6)$ is the pitch angle of rotation of the SECOND SHOULDER JOINT about the pitch axis $\$H(6)=[1,0,0,0,0,0]\$$ is the corresponding axis of rotation. This joint and the previous one are coupled in the sense that the two angles of rotation are equal to each other, so that $\theta(6)=\theta(7)$. $\theta(5)$ is the pitch angle of rotation of the FIRST ELBOW JOINT about the pitch axis. $H(5)=[1,0,0,0,0,0]$ is the corresponding axis of rotation. θ(4) is the pitch angle of rotation of the SECOND ELBOW JOINT about the pitch axis. H(4)=[1,0,0,0,0,0] is the corresponding axis of rotation. This joint and the previous one are coupled in the sense that the two angles of rotation are equal to each other, so that θ(4)=θ(5). θ(3) is the roll angle of rotation of the WRIST about the roll axis H(3)=[0,0,1,0,0,0] is the corresponding axis of rotation. This angle is associated with the FIRST UNIVERSAL JOINT of the wrist. θ(2) is the pitch angle of rotation of the wrist about the pitch axis H(2)=[1,0,0,0,0,0]. θ(1) is the yaw angle of rotation of the WRIST about the yaw axis H(1)=[0,1,0,0,0,0].

Slave Robot: θ(10) is the roll angle of rotation of the TORSO about an axis perpendicular to the base of the manipulator. H(10)=[0,0,1,0,0,0] is the corresponding axis of rotation. θ(9) is the pitch angle of rotation of the FIRST SHOULDER JOINT about the pitch axis. H(9)=[1,0,0,0,0,0]$ is the corresponding axis of rotation. θ(8) is the pitch angle of rotation of the SECOND SHOULDER JOINT about the pitch axis H(8)=[1,0,0,0,0,0] is the corresponding axis of rotation. This joint and the previous one are coupled in the sense that the two angles of rotation are equal to each other, so that θ(8)=θ(9). θ(7) is the pitch angle of rotation of the FIRST ELBOW JOINT about the pitch axis. H(7)=[1,0,0,0,0,0] is the corresponding axis of rotation. θ(6) is the pitch angle of rotation of the SECOND ELBOW JOINT about the pitch axis. H(6)=[1,0,0,0,0,0] is the corresponding axis of rotation. This joint and the previous one are coupled in the sense that the two angles of rotation are equal to each other, so that θ(6)=θ(7). θ(5) the roll angle of rotation of the WRIST about the roll axis H(5)=[0,0,1,0,0,0] is the corresponding axis of rotation. This angle is associated with the FIRST UNIVERSAL JOINT of the wrist. θ(4) is the pitch angle of rotation of the wrist about the pitch axis H(4)=[1,0,0,0,0,0]. This angle is also associated with the FIRST UNIVERSAL JOINT of the wrist. θ(3) is the yaw angle of rotation of the WRIST about the yaw axis H(3)=[0,1,0,0,0,0]. This angle is also associated with the FIRST UNIVERSAL JOINT of the wrist. θ(2) is the yaw angle of rotation of the WRIST about the yaw axis H(2)=[0,1,0,0,0,0]. This angle is associated with the SECOND UNIVERSAL JOINT of the wrist. This angle is identical to the previous one so that θ(2)=θ(3). θ(1) is the pitch angle of rotation of the WRIST about the pitch axis H(1)=[1,0,0,0,0,0]. This angle is associated with the SECOND UNIVERSAL JOINT of the wrist. This angle is identical to the pitch angle of the first universal joint, so that θ(1)=θ(4).

Joint Angles and Axes:

At all of the joints k, there is a coordinate transformation matrix A*(k) defined as follows in terms of the angles of rotation θ(k). When taken sequentially from the base of the manipulator to the tip, these transformations reflect a roll, pitch, pitch, pitch, pitch, roll, pitch, yaw, sequence of rotations for the master robot 8 and a roll, pitch, pitch, pitch, pitch, roll, pitch, yaw, yaw, pitch sequence of rotations for the slave robot 8'.

For the pitch rotations, associated with the set of slave joints k=1, 4, 6, 7, 8, 9, and the master joints k=2, 4, 5, 6, 7, the corresponding rotation matrices are:

$$A^*(k) = \begin{pmatrix} \cos\theta(k) & \sin\theta(k) & 0 \\ -\sin\theta(k) & \cos\theta(k) & 0 \\ 0 & 0 & 1 \end{pmatrix} \quad (1)$$

For the yaw rotations, associated with the slave joints k=2,3 and the master joint k=1, the corresponding rotation matrices are:

$$A^*(k) = \begin{pmatrix} \cos\theta(k) & 0 & -\sin\theta(k) \\ 0 & 1 & 0 \\ \sin\theta(k) & 0 & \cos\theta(k) \end{pmatrix} \quad (2)$$

For the roll rotations, associated with the slave joints k=5,10 and the master joints k=8,3, the corresponding rotation matrices are;

$$A^*(k) = \begin{pmatrix} \cos\theta(k) & \sin\theta(k) & 0 \\ -\sin\theta(k) & \cos\theta(k) & 0 \\ 0 & 0 & 1 \end{pmatrix} \quad (3)$$

The matrix A*(k) transforms any arbitrary vector, expressed in the coordinate system attached to the k+1 link, to the coordinate system attached the k link. This matrix is the transpose of the matrix A(k), which transforms a vector in a coordinate frame attached to link k into a vector expressed in a coordinate frame attached to link k+1.

Link Vectors:

As shown in FIG. 19, the manipulators are composed of a series of links. The links' lengths can vary, but several of the link lengths are preferably zero. Specifically, for the master robot, l2)=l(3)=0, and for the slave robot, l(2)=l(4)=l(5)=0. In fact, these "links" are actually fictitious because they correspond to the joints that have more than one degree of freedom. These joints occur at the universal joints of the wrist. In the preferred embodiment, for the master robot, the wrist universal joint has 3 coincident joints. For the slave robot, the first universal joint is made up of 3 coincident joints, whereas the second universal joint has 2 coincident joints. Further, the compound multi-degree-of-freedom joints can be replaced by an equivalent sequence of single-degree-of-freedom joints. With this arrangement, the distance between consecutive joints vanishes because the joints coincide.

The following 3-dimensional vectors associated with each link are closely related to the link lengths l(k) so that:

$$L(k, k-1) = \begin{pmatrix} 0 \\ 0 \\ l(k) \end{pmatrix} \quad (4)$$

This vector L(k,k−1) goes from joint k to joint k−1, and is expressed in the coordinate system attached to link k.

Absolute Position and Orientation Kinematics:

The following algorithm computes recursively the attitude matrix of a coordinate system attached to the tip of the manipulator, as well as the location of this tip. The tip is defined as being at a distance l(1) away from the base of the output shaft of the second universal joint, measured along the direction of this output shaft.

Algorithm 1:

$$S=U; L=0 \quad (5)$$

where U is the 3×3 unit matrix and L is a 3×1 vector.

loop k = 1, ..., 10

$$S \rightarrow A(k)S; L \rightarrow A(k)L + L(k) \quad (6)$$

end loop.

This algorithm is inwardly recursive and starts at the tip of the manipulator and ends at the base. The matrix S is a 3×3 matrix which accumulates the products of the various transformation matrices A(k). At the termination of the algorithm, the matrix S stores the attitude matrix that transforms tip coordinates to base coordinates. Its transpose S* is a coordinate transformation in the opposite direction. The corresponding vector L stores the location of the tip in base coordinates.

The Spatial Transition Matrices

Associated with each link k, there is a corresponding 6×6 transition matrix $\phi(k,k-1)$ defined in terms of the link vectors L(k,k−1). This matrix is used to propagate quantities, in particular forces, in an inward direction from the k−1 joint to the k joint. Its transpose $\phi^*(k,k-1)$ transforms velocities in the opposite direction from the k joint to the k−1 joint. The transpose $\phi^*(k,k-1)$ is a key quantity in forming the Jacobian for the manipulator, as will be described in the next section.

The general form of the $\phi(k,k-1)$ matrix is:

$$\phi(k, k-1) = \begin{pmatrix} I & \tilde{L}(k, k-1) \\ 0 & I \end{pmatrix} \begin{pmatrix} A(k-1) & 0 \\ 0 & A(k-1) \end{pmatrix} \quad (7)$$

The vector L(k,k−1) is the 3-dimensional vector from joint k to joint k−1, expressed in the "local" coordinate system attached to link k. This vector is used to form the 3×3 matrix $\tilde{L}(k,k-1)$ equivalent to the cross-product operation L(k,k−1)x. The transpose $\phi^*(k,k-1)$ is $$\phi^*(k, K-1) = \begin{pmatrix} A^*(k-1) & 0 \\ 0 & A^*(k-1) \end{pmatrix} \begin{pmatrix} I & 0 \\ -\tilde{L}(k, k-1) & I \end{pmatrix} \quad (8)$$

To go from joint m to joint k, all of the transition matrices along the way from joint m to joint k are multiplied. As an example, $$\phi(6,2) = \phi(6,5)\phi(5,4)\phi(4,3)\phi(3,2) \quad (9)$$

The inverse $\phi^{-1}(k,k-1)$ of $\phi(k,k-1)$ is $$\phi^{-1}(k,k-1) = \phi(k-1,k) \quad (10)$$

Thus, to compute the inverse, the direction of the vector L(k,k−1) is reversed to obtain L(k−1,k), and the definition of this matrix $\phi(k-1,k)$ is used in terms of the link vector L(k−1,k).

Eliminating Redundant Joints

Some of the joints in the manipulators and in the slave wrist are coupled in pairs. These "coupled" joints, together with the corresponding constraints and operations required to "merge" them, are summarized in the following table. For the master robot 8, these are:

| Joint Pair | Constraint | Joint Merging Operation |
|---|---|---|
| Two Shoulder Joints | θ(6) = θ(7) | H(6) → H(6) + H(7)φ(7,6) |
| Two Elbow Joints | θ(4) = θ(5) | H(4) → H(4) + H(5)φ(5,4) |

For the slave robot 8', these are:

| Joint Pair | Constraint | Joint Merging Operation |
|---|---|---|
| Two Shoulder Joints | θ(8) = θ(9) | H(8) → H(8) + H(9)φ(9,8) |
| Two Elbow Joints | θ(6) = θ(7) | H(6) → H(6) + H(7)φ(7,6) |
| Two Wrist Pitch Joints | θ(1) = θ(4) | H(1) → H(1) + H(4)φ(4,1) |
| Two Wrist Yaw Joints | θ(2) = θ(3) | H(2) → H(2) + H(3)φ(3,2) |

The second column in these tables indicate the constraints that pairs of joint angles must satisfy. These constraints result from arrangement of the preferred embodiment of the manipulators and the slave wrist. The two joints in each of the pairs are mechanically coupled to each other. To compute the Jacobian, it is convenient to merge them, in the sense that the joint axis of either one of the two joints in the pair can be replaced by a new joint axis. This new joint axis accounts for the effect of the other joint. For example, consider the process of combining the pair of joints 1 and 4 associated with the two pitch axes of the slave wrist. To combine these two joints, the joint axis H(1) of the first joint is replaced by the "new" joint axis H(1)+H(4) φ(4,1). This new axis takes into account the effects of joint number 4. This merging operation is listed in the next to the last row in the table. Similar operations are listed in the table which merge the other pairs of coupled joints.

These merging operations eliminate redundancies, and the subsequent computation of the Jacobian and its inverse can proceed as though the manipulator had only 6 degrees of freedom. However, the elimination of redundancies outlined above need not always be done, as long as the primary quantity of interest is only the Jacobian. If the sole interest is to compute the Jacobian, this can be done by simply using the second column in the above table. There is no need to use the merging operations in the third column of the table. However, the merging operations are essential in the more common situations in which the Jacobian inverse must be computed.

Recursive Evaluation of the Jacobian and Its Inverse

The following algorithm evaluates the spatial velocity V(k) at any joint k where N is the maximum number of joints on the respective robot (N=10 for the slave robot, N=8 for the master robot):

Algorithm 2:

| | | |
|---|---|---|
| | V(N + 1) = 0 | (11) |
| loop k = N, ..., 1 | | |
| | V(k) = φ*(k + 1, k)V(k + 1) + H*(k)θ(k) | (12) |
| end loop | | |
| | V(0) = φ*(1, 0)V(1) | (13) |

The matrices φ*(k+1,k) and the vectors H(k) are specified in the previous section.

The recursive algorithm above can be used to evaluate each of the columns of the Jacobian matrix. To evaluate the last column, corresponding to the torso joint at the base of the manipulator, the rotation θ(10) for the slave robot and θ(8) for the master robot at the respective joint are set equal to 1, and all of the other joint velocities are set to zero. Then, the recursive algorithm is used to compute the tip velocity V(0). The tip velocity, computed under the assumption that the torso joint is the only rotating joint, is the 6th column of the Jacobian matrix. Similarly, to compute the 5th column, a unit rotation is assumed in the coupled slave joints 8 and 9 and in the coupled master joints 6 and 7 and all of the other rotations are set to zero. The merging operation H(8)→H (8)+H(9) φ(9,8) for the slave and H(6)→H(6)+H(7) φ(7,6) for the master are used to merge joints 8 and 9 for the slave and joints 6 and 7 for the master into an equivalent joint axis located at the 8th slave and 6th master joints. The tip velocity V(0) computed under these assumptions is the 5th column of the Jacobian. All of the other columns are computed using a similar approach, by setting the appropriate joint rates to 1, and by letting the rest of the joint rates be zero. When this is done for every joint, the evaluation of the Jacobian is completed. Inversion of the Jacobian is then be simply achieved by "calling" a matrix inversion subroutine.

Wrist Kinematics

This section analyzes in more detail the kinematics of the wrists. On the slave robot, the wrist preferably consists of 2 universal joints separated by a finite length along the direction of the output shaft of the first universal joint. On the master robot, the wrist preferably consists of a single universal joint and its output shaft is the final link of the robot. The analysis below uses quantities, such as the angular velocity of the output shaft of the first universal joint, to simplify the resulting kinematics equations.

In the description below, the first universal joint refers to the first universal joint of the wrist of the slave robot 8' and the only universal joint of the preferred wrist of the master robot 8. The second universal joint refers to the second universal joint of the wrist of the slave robot 8' and does not refer at all to the master robot 8.

Output Shaft Motion of the 1st Universal Joint with Respect to the Wrist Base:

The first universal joint of the wrist allows 3-axis rotation with respect to the base of the wrist. This rotational motion is characterized by a roll, pitch, yaw sequence of Euler-type angles. This sequence means that, starting from a coordinate system attached to the base of the wrist, there is first a rotation about the roll axis, followed by two consecutive rotations about the pitch and yaw axes.

A coordinate system, characterized by the unit vectors $\hat{a}_1, \hat{a}_2, \hat{a}_3$ is attached to the base of the output shaft of the first universal joint. These unit vectors are orthonormal in the sense that $\hat{a}_i * \hat{a}_j = 0$ for $i \neq j$ and $\hat{a}_i * \hat{a}_i = 1$ for $i=1,2,3$. This coordinate system is related to the coordinate system attached to the base of the wrist by:

$$c \begin{pmatrix} \hat{a}_1 \\ \hat{a}_2 \\ \hat{a}_3 \end{pmatrix} = \begin{pmatrix} C_3 & 0 & -S_3 \\ 0 & 1 & 0 \\ S_3 & 0 & C_3 \end{pmatrix} \begin{pmatrix} 1 & 0 & 0 \\ 0 & C_4 & S_4 \\ 0 & -S_4 & C_4 \end{pmatrix} \begin{pmatrix} C_5 & S_5 & 0 \\ -S_5 & C_5 & 0 \\ 0 & 0 & 1 \end{pmatrix} \begin{pmatrix} \hat{x} \\ \hat{y} \\ \hat{z} \end{pmatrix} \quad (14)$$

where $C_i = \cos\theta(i)$ and $S_i = \sin\theta(i)$.

This sequence of three coordinate transformations are defined in terms of the universal joint angles of the wrist. They are respectively the roll, pitch, and yaw angles of an Euler-type sequence of angles. The unit vectors $\hat{x}, \hat{y}, \hat{z}$ define a coordinate system attached to the base of the wrist.

The Attitude Matrix of the First Universal Joint Output Shaft:

One way to simplify the kinematics of the first universal joint is to use the $\hat{a}_1, \hat{a}_2, \hat{a}_3$ unit vectors to define the attitude matrix $$A = [\hat{a}_1, \hat{a}_2, \hat{a}_3] \quad (15)$$

whose columns are the 3 unit vectors. This matrix can be used to transform any arbitrary vector x defined in the output shaft coordinate into an equivalent vector y=Ax defined in the coordinate system $\hat{x}, \hat{y}, \hat{z}$ attached to the base of the wrist. The third column $\hat{a}_3$ in this matrix is a unit vector in the direction of the output shaft of the first universal joint. The matrix A has a total of nine elements, usually referred to as direction cosines. These nine elements are:

$$\begin{pmatrix} a_{11} & a_{21} & a_{31} \\ a_{12} & a_{22} & a_{32} \\ a_{13} & a_{23} & a_{33} \end{pmatrix} \quad (16)$$

Evolution of the Attitude Matrix:

The attitude matrix moves with an angular velocity $\omega$ expressed in the "body" frame $\hat{a}_1, \hat{a}_2, \hat{a}_3$. This means that the columns $\hat{a}_i$ of the attitude matrix satisfy $$\dot{\hat{a}}_i = w \times \hat{a}_i \quad (17)$$

where $\omega = [\omega_1, \omega_2, \omega_3]$. The angular velocity $\omega$ is a quantity which leads to considerable simplification, of the differential kinematics of the wrist, as outlined in the next section.

Figure 20:
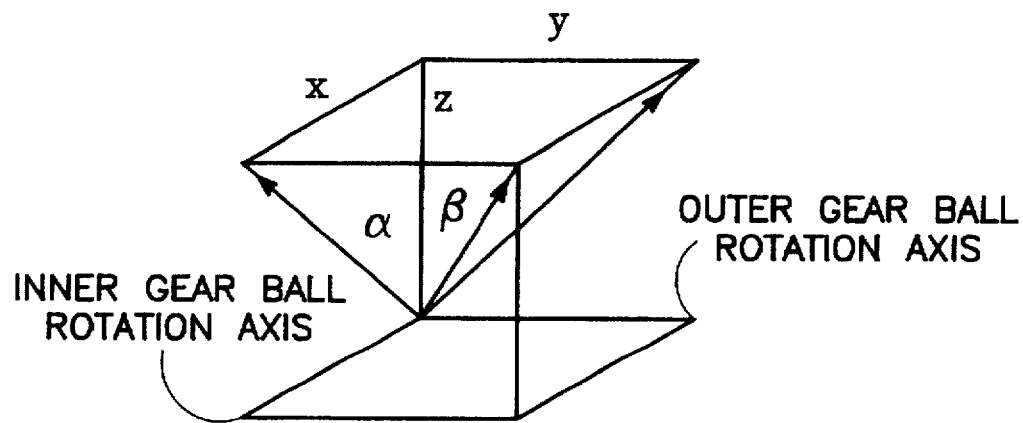
FIG. 20 is a kinematic axes diagram illustrating the gear bail angels and axes of rotation.

Relationships Between the Gear Bail Angles and the Universal Joint Attitude:

FIG. 20 is a kinematic axes diagram illustrating the gear bail angels and axes of rotation. The gear bail angles $\alpha$ and $\beta$ are related to the unit vector $\hat{a}_3$ by the two equations $$\tan\alpha = -\frac{\hat{a}_3 * \hat{y}}{\hat{a}_3 * \hat{z}} \quad ; \quad \tan\beta = \frac{\hat{a}_3 * \hat{x}}{\hat{a}_3 * \hat{a}_3} \quad (18)$$

The equation (18) has a very simple geometrical interpretation illustrated in FIG. 20. Equation 18 provides a means to go from the orientation of the output shaft, as characterized by the unit vector $\hat{a}_3$ to the outer and inner gear bail angles $\alpha$ and $\beta$. In terms of the elements of the attitude matrix.

$$\tan\alpha = -\frac{a_{32}}{a_{33}} \quad ; \quad \tan\beta \frac{a_{31}}{a_{33}} \quad (19)$$

This means that in order to determine the gear bail angles, all that is needed is to select various components of the unit vector $\hat{a}_3 = [a_{31}, a_{32}, a_{33}]$, and then do relatively simple arithmetical operations on these components.

Time Derivatives of the Gear Bail Angles in Terms of the Angular Velocity:

The time derivatives $\dot{\alpha}$ and $\dot{\beta}$ of the gear bail angles are $$\dot{\alpha} = \frac{(a_{33}a_{22} - a_{32}a_{23})\omega_1 + (a_{32}a_{13} - a_{33}a_{12})\omega_2}{a_{33}^2 + a_{32}^2} \quad (20)$$

$$\dot{\beta} = \frac{(a_{23}a_{31} - a_{21}a_{33})\omega_1 + (a_{11}a_{33} - a_{13}a_{31})\omega_2}{a_{33}^2 + a_{31}^2} \quad (21)$$

So, if the attitude matrix A, and the corresponding angular velocity $\omega$ are known, it is relatively easy to simply use the above identities to compute the time derivatives of the gear bail angles. The inverse relationship to compute the derivatives of the gear bail angles from the angular velocity is also relatively simple, as it involves the trivial closed-form inversion of a 2×2 matrix.

Relating the Angular Velocity to the Universal Joint Angle Time Derivatives:

This type of relationship is very well established in classical mechanics. It is analogous to the relationship between the angular velocity of a rigid body and the time derivatives of the corresponding Euler angles. The relationship is:

$$\begin{pmatrix} \omega_1 \\ \omega_2 \\ \omega_3 \end{pmatrix} = \begin{pmatrix} 0 \\ 1 \\ 0 \end{pmatrix} \dot{\theta}(3) + \begin{pmatrix} C_3 \\ 0 \\ S_3 \end{pmatrix} \dot{\theta}(4) + \begin{pmatrix} -C_4 S_3 \\ S_4 \\ C_4 C_1 \end{pmatrix} \dot{\theta}(5) \quad (22)$$

In matrix form, $$\begin{pmatrix} \omega_1 \\ \omega_2 \\ \omega_3 \end{pmatrix} = \begin{pmatrix} 0 & C_3 & -C_4 S_3 \\ 1 & 0 & S_4 \\ 0 & S_3 & C_4 C_3 \end{pmatrix} \begin{pmatrix} \dot{\theta}(3) \\ \dot{\theta}(4) \\ \dot{\theta}(5) \end{pmatrix} \quad (23)$$

This is an equation which computes the angular velocity components $\omega = [\omega_1, \omega_2, \omega_3]$, given the universal joint angle time derivatives $\dot{\theta}(3), \dot{\theta}(4), \dot{\theta}(5)$. The inverse relationship can be obtained in closed-form as follows:

$$\begin{pmatrix} \dot\theta(3) \\ \dot\theta(4) \\ \dot\theta(5) \end{pmatrix} = \frac{1}{C_4} \begin{pmatrix} S_4 S_3 & C_4 & -S_4 C_1 \\ C_4 C_3 & 0 & c_4 S_3 \\ -S_3 & 0 & C_3 \end{pmatrix} \begin{pmatrix} \omega_1 \\ \omega_2 \\ \omega_3 \end{pmatrix} \quad (24)$$

Figure 21:
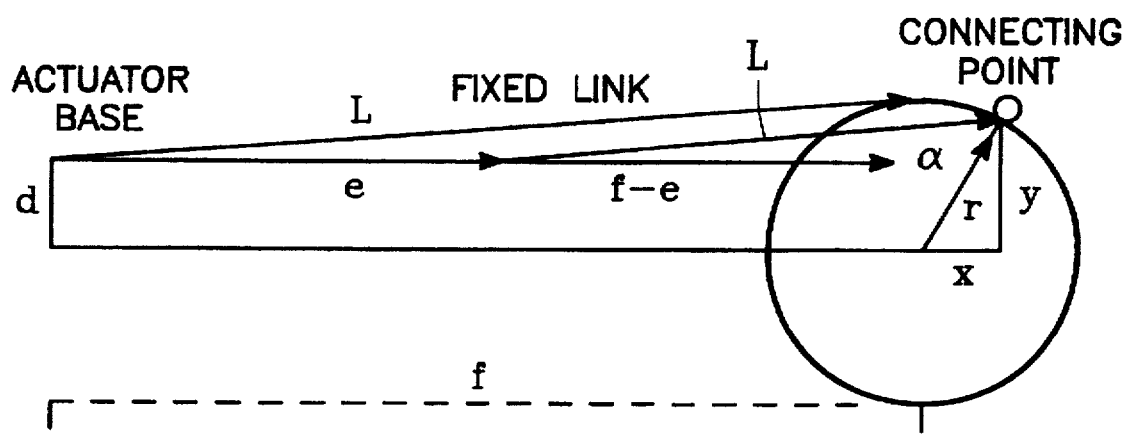
FIG. 21 is a kinematic axes diagram illustrating one of the gear bail angles and rotation due to linear actuation.

Relating Linear Actuator Movement to Gear Bail Angles:

FIG. 21 is a kinematic axes diagram illustrating one of the gear bail angles and rotation due to linear actuation. The pitch and yaw rotation of the wrist is actually achieved by motion of a linear actuator which creates translation along the roll axis at the base of the wrist. The other gear bail angle is handled similarly. In conjunction with FIG. 21, the following Table I defines parameters used in FIG. 21.

TABLE I

| Symbol | Geometrical Meaning | Value |
|---|---|---|
| r | Radius of Circular Bail | Variable |
| d | Distance from Wrist Centerline to Actuator Axis | Variable |
| f | Distance from Actuator Base to Gear Bail Centerpoint | $f = SQRT[l^2 - (r-d)^2]$ |
| L | Length of Link Connecting Actuator to Gear Bail | Variable |
| A | $g^2 + r^2 + d^2 - l^2$ | Variable |
| e | Linear Actuator Displacement | Variable |
| g | f − e | Variable |
| x | x-Coordinate of Connecting Point of Actuating Link and Gear Bail | Variable |
| y | y-Coordinate of Connecting Point of Actuating Link and Gear Bail | Variable |
| α | Gear Bail Angle | Variable |

The goal is to obtain an equation for the gear bail angle α in terms of the linear actuator displacement e. This actuator displacement is the variable which is controlled in order to rotate the gear bail. To this end, the following two simultaneous equations can be written in terms of the unknown coordinates x and y, and the known parameters r, l and g:

$$X^2 + Y^2 = r^2 \quad (25)$$

$$(x-g)^2 + (y-d)^2 = l^2 \quad (26)$$

The parameter g=f−e is viewed as a known parameter because it depends on the fixed parameter f and the control actuator displacement e, which is assumed to be known at any given time. Simultaneous solution of these two equations, leads to the following result:

$$\alpha = ArcTan\ (x/y) \quad (27)$$

where x and y can be computed from known quantities by $$x = \frac{\frac{Ag}{d^2} + SQRT\left[\frac{A^2 g^2}{d^4} - \left(1+\frac{g^2}{d^2}\right)\left(\frac{A^2}{4d^2} - r^2\right)\right]}{2\left(1+\frac{g^2}{d^2}\right)} \quad (28)$$

$$y = SQRT[r^2 - x^2] \quad (29)$$

Alternative Approach

Figure 22:
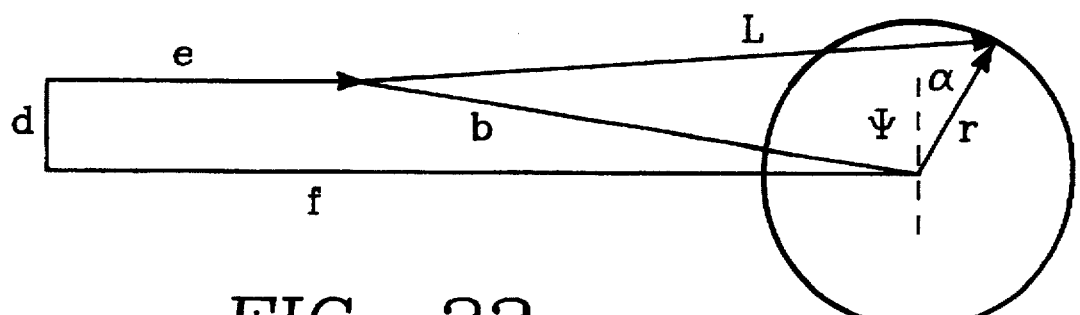
FIG. 22 is a kinematic axes diagram illustrating a streamlined approach to relating the linear actuator movement e to the gear bail angle α.

FIG. 22 is a kinematic axes diagram illustrating a streamlined approach to relating the linear actuator movement e to the gear bail angle α and is outlined below. The linear actuator displacement e causes a change in the vector b defined as $$b = f + d + c \quad (30)$$

The other two components f and d of this vector do not change, and are fixed geometrical quantities. In FIG. 22, focus on the triangle formed by the vectors b, L and r, which satisfy $$L = b - r \quad (31)$$

The objective is to find the angle ψ between the vectors b and r. It should be noted that:

$$|L|^2 = |b|^2 + |r|^2 - 2|r||b|\cos\psi \quad (32)$$

This implies that:

$$\psi = ArcCos\left[\frac{|b|^2 + |r|^2 - |L|^2}{2|r||b|}\right] \quad (33)$$

This determines the angle ψ in terms of quantities that are fixed, except for the linear actuator displacement e which is a time-dependent controlled quantity. The angle ψ−α that the vector b makes with the vertical axis is determined by:

$$\psi - \alpha = ArcTan\ [|g|/|d|] \quad (34)$$

Since ψ is known from Equation (33), this determines the gear bail angle α.

The algorithms just summarized are the key components of the kinematic control algorithms used for the slave robot 8'. In particular, Algorithm 1 is used for absolute kinematics, while Algorithm 2 is used for computing and inverting the Jacobian.

Figure 23:
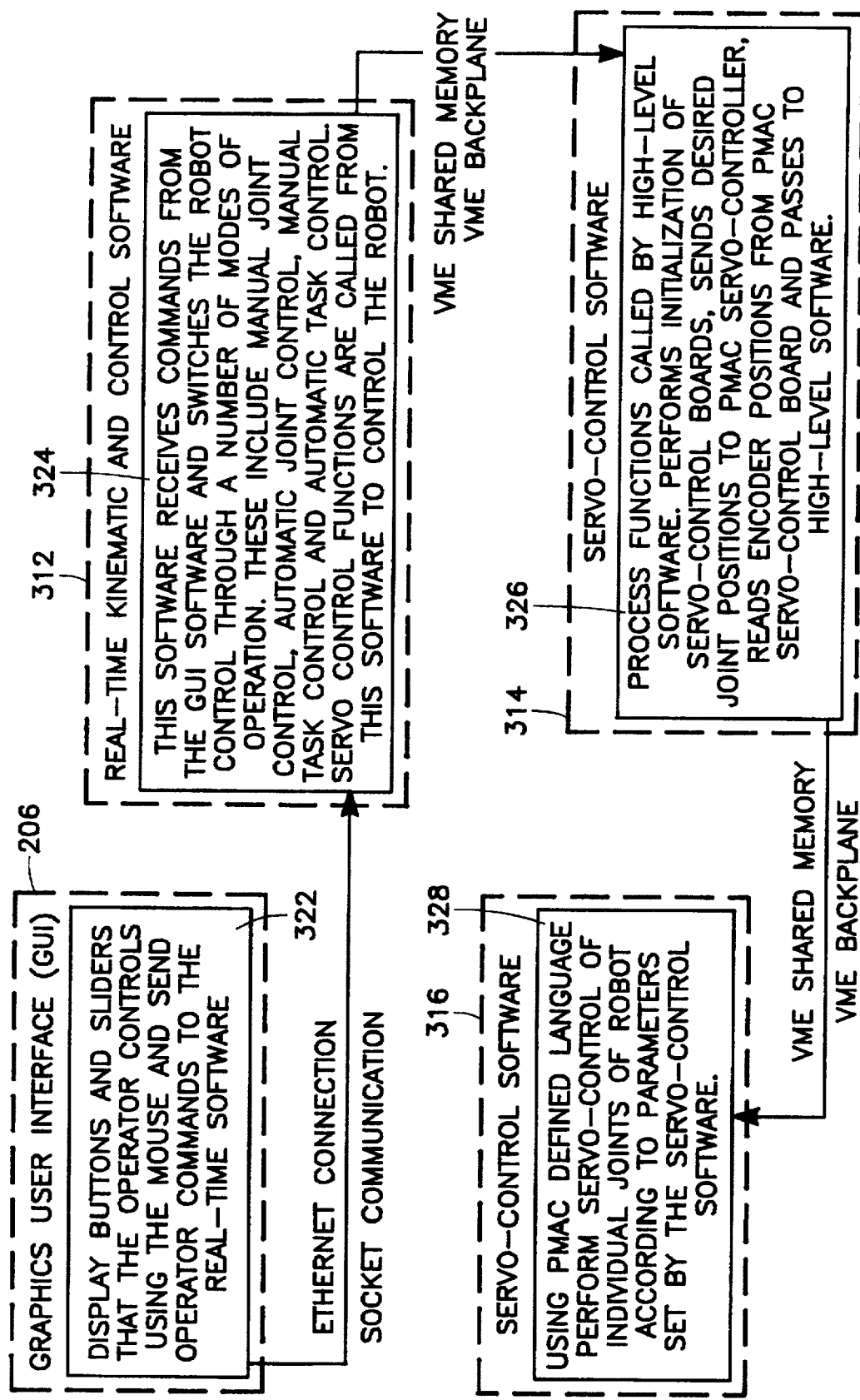
FIG. 23 is a block diagram illustrating an overview of the high-level software architecture.

High-level Software Sub-system:

FIG. 23 is a block diagram illustrating an overview of the high-level software architecture. There are two components to the real-time software. The components include a state transition controller (described in FIG. 25 below) and computation executions (which can include many different executions, including custom executions, depending on the application). Some components with computation executions are described in application Ser. No. 08/525,813 filed Sep. 7, 1995 by Ohm et al. entitled "A DECOUPLED SIX DEGREE-OF-FREEDOM ROBOT MANIPULATOR", which application is incorporated herein by reference. These components may be implemented in a programming language, for example, C or C++ or more easily with a real-time software development environment, such as, Real-time Innovation Inc.'s Control Shell.

Embedded in the computational blocks of the real-time control software are the kinematic control algorithms. The kinematics of the robot system and the algorithms used to compute its forward and inverse kinematics are described above. The system is capable of demonstrating different control modes of the robot and handling operator commands in real-time, transitions between states of control, and changes in data flow due to transitions of states in the software. A state corresponds to a subset of software computational modules used to perform computations for it.

The high-level software has two components, graphics user interface software 322 and real-time kinematic and control software 324. The graphics user interface software 322 produces a graphics user interface (GUI) residing on the Unix host machine 206. The GUI 322 interacts with the user and communicates user input to the MVME167 Proc0 board 312 through the socket interface. The UNIX workstation 206 is coupled to the MVME167 Proc0 board in the VME chassis through, for example, an Ethernet connection, as described above in FIG. 16. The real-time kinematic and control software 324 is implemented on the MVME167 Proc0 board 312.

Specifically, the GUI 322 displays buttons and sliders that the user controls using an input device, such as a mouse. The two components 322, 324 have input and output communication channels implemented for message passing between the two components 322, 324. The software could be, for example, using the UNIX socket utility or Real-time Innovation, Inc.'s NDDS.

The real-time kinematic control software 324 of the high-level control software runs on the MVME167 Proc0 board 312 in the VME chassis and receives user commands input to the GUI 322 in real-time. Also, the real-time kinematic control software 324 switches control of the robot through a number of modes of operation. These modes of operation include manual joint control, automatic joint control, manual Cartesian control, and automatic Cartesian control. In all of these modes, servo control functions are called from the real-time software to control the robot.

A servo-control software module 326 runs on the MVME167 Proc1 board 314 in the VME chassis. The servo-control software module 326 processes functions called by the high-level software, performs initialization of servo-control boards, sends desired joint positions to the PMAC servo-controller, reads encoder positions from PMAC servo-controlled board, and sends the information back to the high-level software. A servo-controller 328 resident on the PMAC boards 316 performs servo-control of individual joints of the robot according to parameters set by the servo-control software module. It should be noted that the servocontrol software module and the servo-controller on the PMAC boards can have shared memory through the VME backplane.

Figure 24:
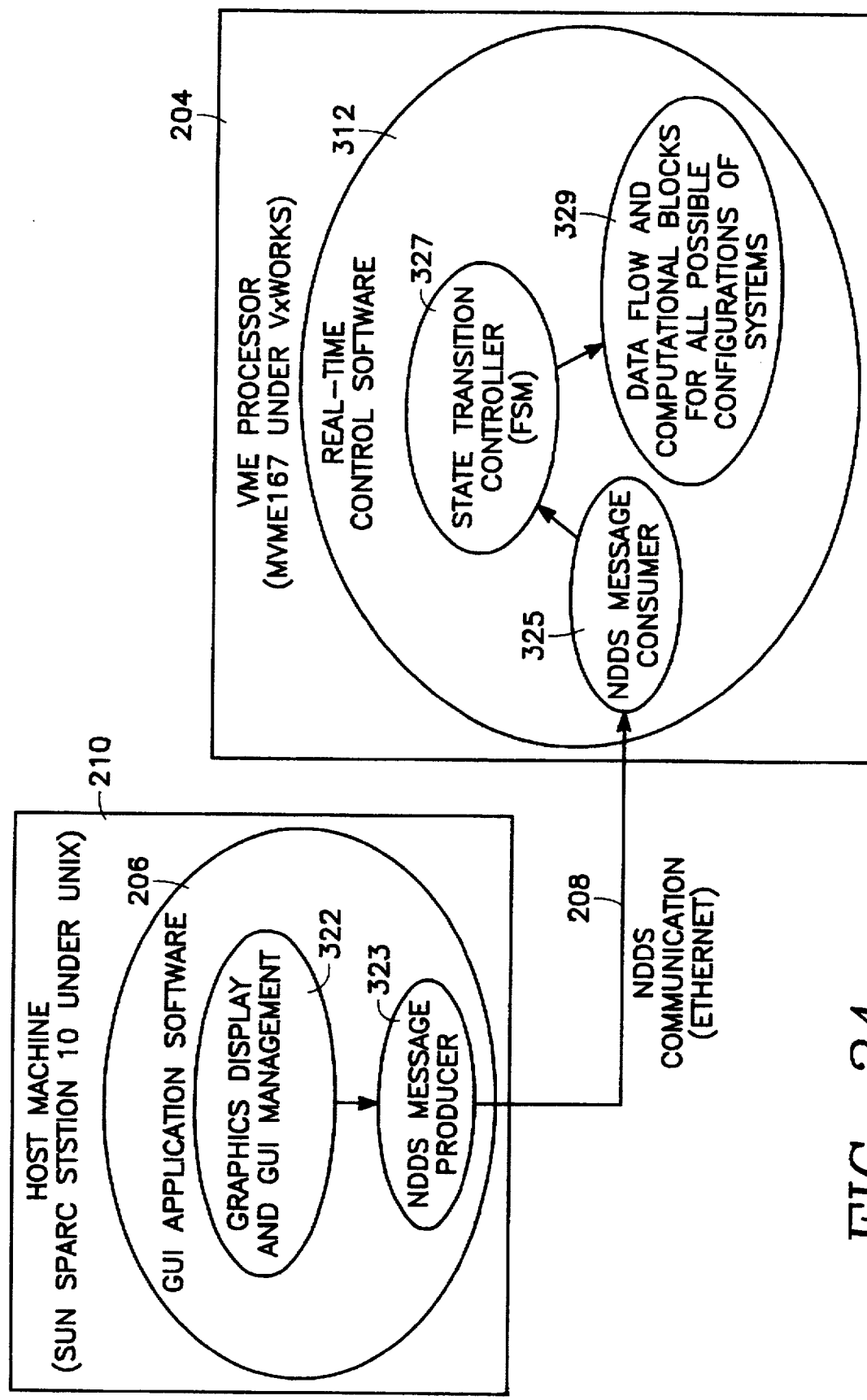
FIG. 24 is a block diagram illustrating the specific interaction between the workstation and the control chassis.

FIG. 24 is a block diagram illustrating the specific interaction between the workstation and the control chassis. The real-time control software 312 includes a GUI message reception and processor 323, such as the NDDS socket utility message producer described above, a state transition controller 327 with a number of states implemented corresponding to different demonstration modes of the robot, and a set of computational modules 329 that implement algorithms connected by data flow paths. Each state corresponds to a subset of the computational modules and data flow paths.

Commands entered into the GUI 322 are transmitted over the Ethernet connection 208 and are received by the control chassis 204. Messages are created by the message reception and processor 323. Message structure is preferably predefined. Each message preferably has a header code indicating the transition requested and parameters that quantify the transition. At the start-up of the software, the NDDS is initialized. Thereafter, any GUI 322 interaction that is to generate a message to the real-time software calls a callback routine that sets up the message data structure and runs the NDDS producer 323 to produce the message.

The messages are broadcast from the workstation 210 to a NDDS message consumer processor 325 of the control chassis 204 via the Ethernet connection 208. The control chassis 204 processes the messages by first having the consumer processor 325 receive and monitor the messages. Messages received are converted into a corresponding stimulus to the state transition controller 327, such as a FSM controller, with accompanying parameters defining the transition. Last, data flow and computational blocks for all possible configurations of the system are generated by the computational modules 329.

Figure 25:
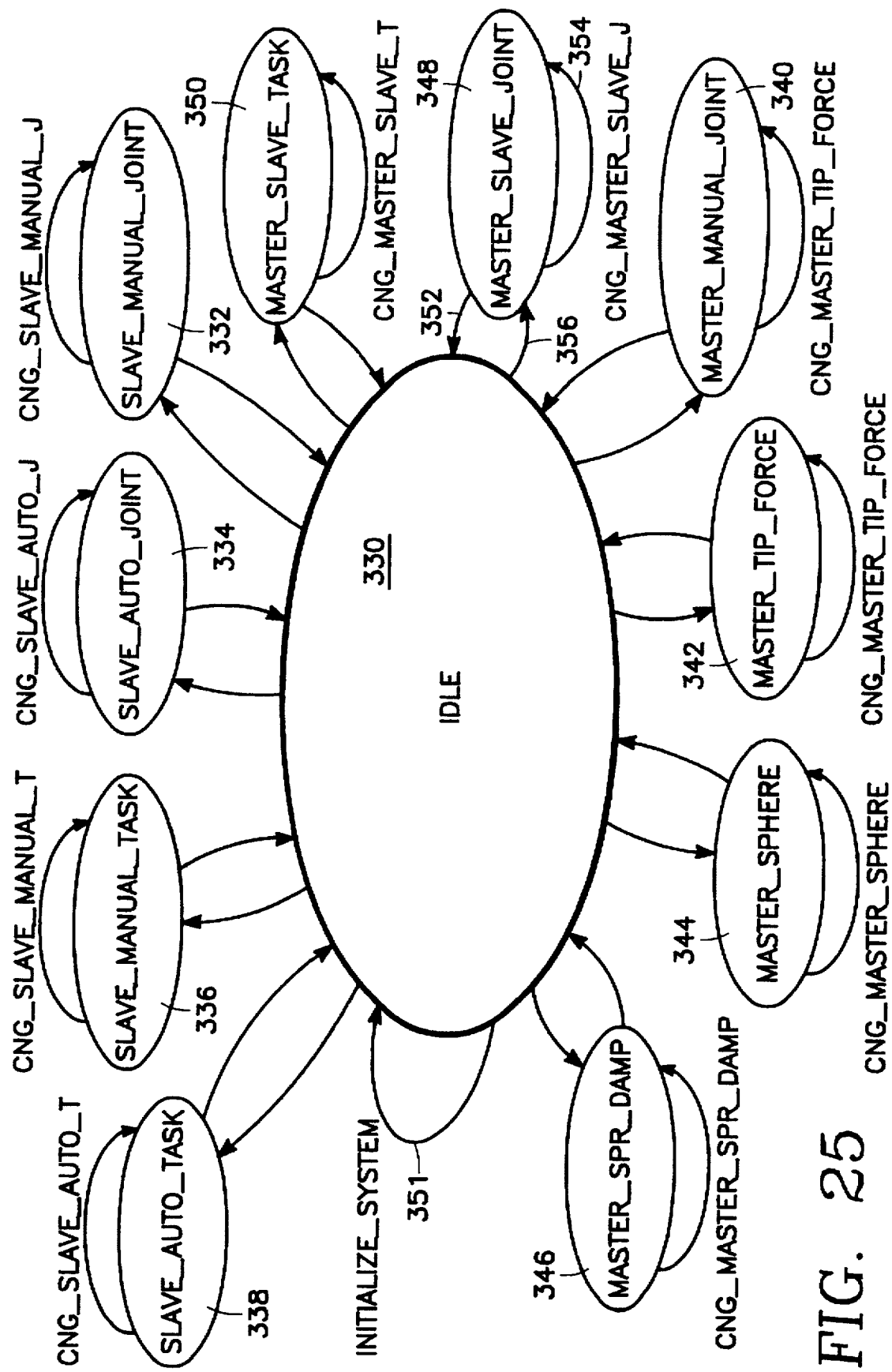
FIG. 25 is a block diagram illustrating the states and their possible transitions in the real-time high-level software architecture.

FIG. 25 is a block diagram illustrating the states and their possible transitions in the real-time high-level software architecture. Referring to FIGS. 23 and 24 along with FIG. 25, during a transition initiated by an operator of the system, set-up routines are executed and data flow paths are re-configured for the new state. Transitions in state are initiated by the operator from the GUI 322 part of the system. The consumer processor 325 of the real-time control software 312 monitors messages received from the GUI 322 through the communication channel 208 using the NDDS protocol.

The states implemented in the control of the slave 8' robot are: an idle state 330, a manual joint control state 332, an autonomous joint control state 334, a manual task control state 336, and an autonomous task control state 338. The idle state 330 is where the slave robot joints are controlled to hold its current position. The manual joint control state 332 is for implementing a manual control mode of the slave robot in joint space using the keyboard/mouse as the input device.

Also, the autonomous joint control state 334 is autonomous repetitive sinusoidal motion in joint space exercising selected joints of the slave robot. The manual task control state 336 is for implementing a manual control mode of the slave robot in Cartesian space coordinates using the keyboard/mouse as the input device. The autonomous task control state 338 is autonomous repetitive sinusoidal motion exercising selected in Cartesian space coordinates of selected coordinates of the slave robot.

The states implemented in the control of the master robot 8 are: a manual joint control state 340, tip force control state 342, a sphere control state 344, a spring damper control state 346, a slave joint control state 348, and a slave task control state 350. The manual joint control state 340 is for implementing a manual control mode of the master robot in joint space using the keyboard/mouse as the input device. The tip force control state 342 is for implementing a manual force control mode of the slave robot in Cartesian space coordinates using the keyboard/mouse as the input device. The sphere control state 344 is for implementing a simulated spherical wall environment around the input device that applies a force to the user's hand operating the master robot to keep the hand motions within a spherical region centered on the start position.

In addition, the spring damper control state 346 is for implementing a simulated spring/damper environment that applies forces on the user's hand operating the master robot to give it the feeling that it is moving the handle that is attached to a spring and damper in a parallel arrangement. The slave joint control state 348 is for implementing control of the slave robot using the master device so that moving joints on the master commands motion for its corresponding joints on the slave. The slave task control state 350 is for implementing master to slave teleoperated control so that Cartesian space motion of the master robot is replicated at the slave tip.

The state transition that starts from the idle state 330 performs initialization 351 of the servo-control system and returns to the idle state 330. This transition is performed automatically at the initialization of the real-time software set-up and is preferably not controlled manually from the GUI. Thus, when the system is initialized 351, the system returns 352 to the idle state 330.

Within each state, changes 354 can be made to accommodate a user's particular input. For example, transitions from one state to another can be performed in response to messages from the GUI 322 of FIGS. 23–25. Also, transitions can be made to change states or return to the same state after a change of parameters. Further, state transition from the idle state 330 to a particular state is achieved by a goto state transition command 352. For example, a state transition that starts from the idle state 330 performs set-up of data component modules and data and re-configures the system to the desired state.

Robot Operation:

The robot is started by powering the VME chassis, thereby initiating the down-loading and running of software on the MVME167 boards and PMAC boards. The GUI program is then run on the UNIX host machine to start-up the graphics user interface and establish communication between the UNIX host and the MVME167 board using the NDDS facility. A procedure of phasing the motors is performed after the boot-up sequence and powering up the amplifier chassis. The system is then ready for demonstrating the various control modes available. During the demonstration modes of control, the high-level software computes the desired joint positions for the robot. These are fed to the PMAC board by the servo-control software. The control loop within the PMAC board reads the actual joint positions and applies the appropriate voltages to the motors to drive the joints to the desired positions. The motors, in turn, drive gears that rotate the spools of cables on the robot so that the joints move in the desired motion.

What is claimed is:

1. A robot manipulator coupled to an external device, said robot manipulator comprising:

an actuator base with plural actuators said actuator base having means for receiving forces generated by said external device;

an end effector interactive with an operator;

a force feedback sensor coupled between said end effector and said actuator base for receiving said forces from said actuator base, converting said forces into feedback forces, and providing said feedback forces to said operator;

plural arms extending seriatim between said end effector and said actuator base;

plural joints connected between pairs of adjacent arms;

wherein each one of said plural joints comprises means for mechanically coupling respective ones of said actuators to respective ones of said joints through intermediate ones of said joints, and wherein said means for mechanically coupling is decoupled from said intermediate joints;

a user interface for receiving user commands;

a servo controller coupled to said arm and wrist joints for reading actual positions of said arm and wrist joints; and a real-time kinematic processor coupled to said user interface and said servo controller for receiving said user commands and said actual positions of said arm and wrist joints, for computing forward and inverse kinematic relationships and for controlling said arm and wrist joints in accordance with said user commands and said computed relationships.

2. The invention as set forth in claim 1, wherein said external device is a slave manipulator.

3. The invention as set forth in claim 1, wherein said external device is a programmed processor for producing fictitious forces.

4. The invention as set forth in claim 3, wherein said means for mechanically coupling comprises:

a first keying drive component coupled to a second keying drive component;

a first passing drive component coupled to respective ones of said actuators for receiving rotational motion; and a second passing drive component coupled to said first passing drive component for receiving said rotational motion from said first passing drive component and for transmitting said received rotational motion to one of said plural joints;

wherein said first and second keying drive components are constrained to rotate about one another to define an instantaneous center of rotation;

wherein said first passing drive component rotates with respect to said second passing drive component about said instantaneous center of rotation.

5. The invention as set forth in claim 4, wherein said first keying drive component is a first keying pulley and said second keying drive component is a second keying pulley.

6. The invention as set forth in claim 5, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

7. The invention as set forth in claim 4, wherein said first and second keying drive components are keying spur gears.

8. The invention as set forth in claim 4, wherein said first and second passing drive components are passing spur gears.

9. The invention as set forth in claim 4, wherein said first passing drive component is a first passing pulley and said second passing drive component is a second passing pulley.

10. The invention as set forth in claim 9, further comprising plural passing cables for rotatably coupling said first passing pulley to said second passing pulley and for rotationally constraining said first passing pulley to said second passing pulley so that said first and second passing pulleys rotate with respect to one another about said instantaneous center of rotation.

11. The invention as set forth in claim 3, wherein all actuators drives of said manipulator are located within said actuator base.

12. The invention as set forth in claim 3, wherein each of said joints comprises dual independent antibacklash drive transmission preloaded with respect to one another.

13. The invention as set forth in claim 3, wherein said plural joints further comprises an antibacklash mechanism for transmitting motion without backlash from respective ones of said plural actuator drives to respective ones of said joints, said antibacklash mechanism comprising:

at least a first transmission stage comprising first dual drive components, wherein both of said first dual drive components are rotatably coupled to said respective ones of said plural actuator drives and are independently rotatable with respect to one another; and at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said plural actuator drives is transmitted through said first and second stages, to said respective ones of said joints without backlash.

14. The invention as set forth in claim 1, further comprising a universal joint coupled to said end effector.

15. The invention as set forth in claim 1, wherein said universal joint includes dual bearing rings attached to pitch and yaw actuation links to provide decoupling of said pitch and yaw actuation links and zero backlash in all axes.

16. A robot manipulator system, comprising:

a slave manipulator coupled to a master manipulator, each of said manipulators comprising, an actuator base with plural actuators, an end effector, plural arms extending seriatim between said respective end effector and said respective actuator base, and plural joints connected between pairs of respective adjacent arms;

wherein said master manipulator further comprises a force feedback sensor coupled between said end effector and said actuator base for receiving forces from said slave manipulator, converting said forces into feedback forces, and providing said feedback forces to an operator; and wherein each one of said plural joints of said slave and master manipulators comprises means for mechanically coupling respective ones of said actuators to respective ones of said joints through intermediate ones of said joints, and wherein said means for mechanically coupling is decoupled from said intermediate joints.

17. The invention as set forth in claim 16, wherein said means for mechanically coupling comprises:

a first keying drive component coupled to a second keying drive component;

a first passing drive component coupled to respective ones of said actuators for receiving rotational motion; and a second passing drive component coupled to said first passing drive component for receiving said rotational motion from said first passing drive component and for transmitting said received rotational motion to one of said plural joints;

wherein said first and second keying drive components are constrained to rotate about one another to define an instantaneous center of rotation;

wherein said first passing drive component rotates with respect to said second passing drive component about said instantaneous center of rotation.

18. The invention as set forth in claim 17, wherein said first keying drive component is a first keying pulley and said second keying drive component is a second keying pulley.

19. The invention as set forth in claim 18, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

20. The invention as set forth in claim 17, wherein said first and second keying drive components are keying spur gears.

21. The invention as set forth in claim 17, wherein said first and second passing drive components are passing spur gears.

22. The invention as set forth in claim 17, wherein said first passing drive component is a first passing pulley and said second passing drive component is a second passing pulley.

23. The invention as set forth in claim 17, wherein all actuators drives of said manipulator are located within said actuator base.

24. The invention as set forth in claim 16, further comprising plural passing cables for rotatably coupling said first passing pulley to said second passing pulley and for rotationally constraining said first passing pulley to said second passing pulley so that said first and second passing pulleys rotate with respect to one another about said instantaneous center of rotation.

25. The invention as set forth in claim 16, wherein each of said joints comprises dual independent antibacklash drive transmission preloaded with respect to one another.

26. The invention as set forth in claim 16, wherein said plural joints further comprises an antibacklash mechanism for transmitting motion without backlash from respective ones of said plural actuator drives to respective ones of said joints, said antibacklash mechanism comprising:

at least a first transmission stage comprising first dual drive components, wherein both of said first dual drive components are rotatably coupled to said respective ones of said plural actuator drives and are independently rotatable with respect to one another; and at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said plural actuator drives is transmitted through said first and second stages, to said respective ones of said joints without backlash.

27. The invention as set forth in claim 16, further comprising a universal joint coupled to said end effector.

28. The invention as set forth in claim 16, wherein said universal joint includes dual bearing rings attached to pitch and yaw actuation links to provide decoupling of said pitch and yaw actuation links and zero backlash in all axes.

29. The invention as set forth in claim 16, wherein each of said respective actuator base comprising plural motors and plural encoders.

30. The invention as set forth in claim 29, further comprising:

a control chassis coupled to said respective encoders of said master and slave manipulators;

a workstation coupled to said control chassis; and an amplifier chassis coupled to said control chassis and said respective motors of said master and slave manipulators to precisely emulate movement of said master manipulator by said slave manipulator.

31. A multiple degree of freedom microsurgical robot manipulator, comprising:

a slave manipulator coupled to a master manipulator, each of said manipulators comprising, a plurality of miniaturized decoupled robot joints comprising a plurality of arm joints each having a first keying pulley constrained to rotate about a second keying pulley, thereby defining an instantaneous center of rotation to effectuate one degree of freedom movement, and a miniaturized wrist joint coupled to one of said arm joints and having a tip and three degrees of freedom;

a plurality of miniaturized driving cables, each coupled an actuator drive at a proximal end and coupled to one of said joints at a distal end; and a computer control system coupled between said master and said slave manipulators for precisely emulating movement of said master manipulator by said slave manipulator.

32. The invention as set forth in claim 31, wherein each of said actuator drives comprises a plurality of motors with rotational motion and having optical encoders for effecting micro-rotation of said motors and for transmitting said rotational motion of said motors to said driving cables.

33. The invention as set forth in claim 32, wherein said robot further comprises an antibacklash mechanism for transmitting motion without backlash from respective ones of said actuator drives to respective ones of said joints, said antibacklash mechanism comprising:

- at least a first transmission stage comprising first dual drive components, wherein both of said first dual drive components are rotatably coupled to said respective ones of said actuator drives and are independently rotatable with respect to one another; and
- at least a second transmission stage comprising second dual drive reduction means, wherein each one of said second dual drive reduction means is rigidly attached to one of said first dual drive components and is rotatably coupled to said respective ones of said joints, whereby rotational motion of said respective ones of said actuator drives is transmitted through said first and second stages, to said respective ones of said joints without backlash.

34. The invention as set forth in claim 31, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

35. The invention as set forth in claim 31, wherein said first and second keying pulleys are keying spur gears.

* * * * *